US012797597B2

(12) United States Patent
Mertens et al.

(10) Patent No.: US 12,797,597 B2
(45) Date of Patent: Nov. 17, 2026

(54) AUTOMATIC WELD/RESET MOTION OF CLAMPS AFTER CLAMP CLOSING/OPENING AND TUBE REMOVAL

(71) Applicant: Terumo BCT, Inc., Lakewood, CO (US)

(72) Inventors: Wilfried Mertens, Hasselt (BE); Filip Paeps, Leefdaal (BE); Philip Madden, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 292 days.

(21) Appl. No.: 18/438,649

(22) Filed: Feb. 12, 2024

(65) Prior Publication Data

US 2024/0325714 A1 Oct. 3, 2024

Related U.S. Application Data

(60) Provisional application No. 63/455,873, filed on Mar. 30, 2023.

(51) Int. Cl.
*A61M 39/14* (2006.01)
*A61M 39/10* (2006.01)

(52) U.S. Cl.
CPC ...... *A61M 39/146* (2013.01); *A61M 39/1011* (2013.01); *A61M 2039/1044* (2013.01); *A61M 2205/33* (2013.01)

(58) Field of Classification Search
CPC ................ A61M 39/146; A61M 39/18; A61M 39/1011; A61M 2039/1044; A61M 2205/33; B29C 66/5221; B29C 66/857; B29C 66/0242
USPC ..................... 156/64, 304.2, 378, 304.6, 503
See application file for complete search history.

(56) References Cited

U.S. PATENT DOCUMENTS

| | | | | |
|---|---|---|---|---|
| 4,521,263 | A * | 6/1985 | Benin ................. | A61M 39/146 604/905 |
| 6,026,882 | A | 2/2000 | Yamada et al. | |
| 6,460,592 | B1 | 10/2002 | Sano et al. | |
| 2020/0223154 | A1 | 7/2020 | Kanemaru | |

FOREIGN PATENT DOCUMENTS

| | | | |
|---|---|---|---|
| EP | 1048316 | B1 | 10/2003 |
| EP | 1640142 | A1 | 3/2006 |
| EP | 1346749 | B1 | 3/2009 |

(Continued)

OTHER PUBLICATIONS

International Search Report and Written Opinion issued in PCT/US2024/018021, mailed Aug. 8, 2024; (14 pages).

*Primary Examiner* — John L Goff, II
(74) *Attorney, Agent, or Firm* — Harness, Dickey & Pierce, P.L.C.

(57) ABSTRACT

A tube-joining device for joining two flexible tube sections including a tube holder configured to hold the flexible tube sections in place for joining. The tube holder may have a clamped and a non-clamped configuration. The tube holder may have a start and a finish configuration. The tube holder may have tube detectors. When certain criteria are met, the tube holder may automatically begin a tube-joining operation, or may automatically return itself from the finish to the start configuration, or the tube-joining device may automatically begin heating a blade used for cutting and melting the tubes.

11 Claims, 12 Drawing Sheets

(56) References Cited

FOREIGN PATENT DOCUMENTS

| | | | | |
|---|---|---|---|---|
| WO | WO-2020262192 A1 * | 12/2020 | .............. | A61M 1/28 |
| WO | WO-2021188049 A1 * | 9/2021 | ......... | B29C 65/2061 |
| WO | 2022/256404 A1 | 12/2022 | | |

* cited by examiner

AUTOMATIC WELD/RESET MOTION OF CLAMPS AFTER CLAMP CLOSING/OPENING AND TUBE REMOVAL

CROSS-REFERENCE TO RELATED APPLICATIONS

This application claims the benefit of U.S. Provisional Application No. 63/455,873, filed on Mar. 30, 2023. The entire disclosure of the above application is incorporated herein by reference.

FIELD

The present disclosure relates to devices and methods for joining flexible tubes for use in bags for containing blood or blood components.

BACKGROUND

This section provides background information related to the present disclosure which is not necessarily prior art.

Blood bags may be used to collect and store blood or blood components obtained from donated blood. A blood bag typically includes a flexible plastic pouch connected to one end of a flexible tube. When the blood is not being accessed (e.g., when the blood bag is in storage) the blood bag may be sealed by a weld at a free end of the flexible tube. When the blood needs to be accessed, the flexible tube may be connected to a blood transfusion system, a dialysis system, and the like. To access the blood when the blood bag is connected to one of these systems, the free end of the flexible tube must be cut.

Often, the blood contained in the blood bag is accessed for further processing and further storage. For example, the blood stored may be separated into different components (e.g., plasma, red blood cells, white blood cells, etc.) by centrifugal separation. After being separated by centrifugation, the individual blood component may be drawn from the blood bag and transferred to another blood bag for storage or further use. Blood bags containing different blood components may thus be produced, packaged, and supplied as needed. When the blood component is needed, the flexible tube of the blood bag containing the separated blood component may be cut and connected to a piece of medical equipment such as those listed above.

Whichever the purpose of accessing the blood or blood component in the blood bag, it is necessary to cut away the weld at the free end of the flexible tube and connect it to another tube. For reasons of medical safety, the cutting and the connecting must be performed under sterile conditions. Typically, the new connection may be formed by welding the flexible tube of the blood bag to another flexible tube, which can provide a leak-free connection and good mechanical strength.

Tube-joining devices may be used for joining together two flexible tubes. In general, the two flexible tubes to be joined are installed into the tube-joining device in parallel next to each other. The tube-joining device, by way of a heated blade, then cuts the flexible tube sections and melts the cut faces. The tube-joining device then displaces the flexible tube sections on one side of the blade so that a cut face of one tube is aligned with a cut face of the other tube. Upon withdrawal of the blade, the cut face of one tube is allowed to contact the cut face of the other tube, thereby forming a welded joint. The flexible tube sections are then released from the device.

Conventionally, a number of inputs from an operator of the tube-joining device are necessary during a tube-joining operation. At a minimum, the operator is required to install flexible tube sections into the tube-joining device before a tube-joining operation and, after the tube-joining operation, remove the flexible tube sections from the tube-joining device. The operator, however, may also be required to push a button on the tube-joining device to cause it to begin heating the blade. Afterwards, it may take some time for the blade to heat up to a temperature sufficient for cutting and melting the material of the flexible tube sections before a tube-joining operation may begin. Following this, the operator may be required to push a button to cause the tube-joining device to begin the tube-joining operation.

In addition, the operator may be required, after a tube-joining operation, and after the flexible tube sections have been removed from the tube-joining device, to push a button to cause the tube-joining device to reset itself for the next tube-joining operation. Thus, with conventional tube-joining devices, the steps required to join flexible tube sections are numerous, and the tube-joining device may require a substantial amount of time to perform each of these steps. Accordingly, there is a desire to reduce the number of operations performed by the operator, and to reduce total time required to perform a tube-joining operation.

SUMMARY

This section provides a general summary of the disclosure, and is not a comprehensive disclosure of its full scope or all of its features.

According to a first aspect, the present disclosure provides tube-joining device (10) for joining two flexible tube sections (16, 18). The device includes a controller (12); a tube holder (14) configured to hold the flexible tube sections (16, 18) in place for joining, the tube holder (14) having a clamped configuration (**26*b*) whereby any flexible tube sections (16 or 18) held in the tube holder (14) are clamped; and wherein upon receipt by controller (12) of a signal indicative of the tube-joining device (14) being in the clamped configuration (26*b*), the controller (12) is configured to automatically start a tube-joining operation to join the two flexible tube sections (16, 18**).

According to the first aspect, the tube holder (14) further comprises a first tube detector (40) in communication with controller (12) that is configured to generate a signal indicative of whether a first tube section (16 or 18) is present the tube holder (14); and wherein the controller (12) upon receipt of the signal from the first tube detector (40) that the first tube section (16 or 18) is present in the tube holder (14) is configured to start the tube-joining operation.

According to the first aspect, the tube holder comprises (14) a second tube detector (42) in communication with the controller (12) that is configured to generate a signal indicative of whether a second tube section (16 or 18) is present in the tube holder (14); and wherein the controller (12) upon receipt of the signal from the second tube detector (42) that the second tube section (16 or 18) is present in the tube holder (14) is configured to start the tube-joining operation.

According to the first aspect, the first and second tube detectors (40, 42) are located proximate the tube holder (14) such that, after the tube-joining operation, each of the first and second tube detectors (40, 42) are configured to generate a signal indicative of a presence of a joined tube.

According to the first aspect, the tube-joining device further comprises a blade (20) that is configured to cut the flexible tube sections (16, 18); and a heat source (36) in communication with the controller (12), wherein the heat source (36) is configured to heat the blade (20) up to a tube-joining temperature based on an instruction received from the controller (12).

According to the first aspect, the tube-joining device further comprises a temperature monitor (44) in communication with the controller (12) and configured to generate a signal indicative of a temperature of the blade (20); and wherein the controller (12) is configured to prevent the tube-joining device (10) from starting the tube-joining operation until receiving the signal indicative of the temperature of the blade (20) from the temperature monitor (44) that the temperature of the blade (20) is at the tube-joining temperature.

According to the first aspect, the tube holder (14) is configured to be in a start configuration (46*a*) before executing a tube-joining operation, and wherein the tube holder (14) is configured to be in a finish configuration (46*b*) after executing the tube-joining operation; wherein the tube-joining device (10) comprises a first tube detector (40) in communication with the controller (12) that is configured to generate a signal indicative of whether a first tube section (16 or 18) is present in the tube holder (14); and wherein the controller (12) is configured to instruct a motorized mechanism (22) to return the tube holder (14) from the finish configuration (46*b*) to the start configuration (46*a*) when the first tube detector (40) generates a signal indicative of the first tube section (16 or 18) not being present.

According to the first aspect, the tube holder (14) is configured to be in the clamped configuration (26*b*) by a manual operation.

According to the first aspect, the tube holder (14) comprises a clamp (32), and the manual operation includes closing the clamp (32).

According to the first aspect, the controller (12) is configured to instruct a motorized mechanism (58) to move the tube holder (14) to be in the clamped configuration (26*b*) automatically after the controller (12) has received a signal indicative that flexible tube sections (16, 18) are located in the tube holder (14).

According to a second aspect of the present disclosure, there is provided a tube-joining device (10) for joining two flexible tube sections (16, 18), the device comprising a controller (12); a tube holder (14) configured to hold the flexible tube sections (16, 18) in place for joining, wherein the tube holder (14) is configured to be in a start configuration (46*a*) before executing a tube-joining operation, and wherein the tube holder (14) is configured to be in a finish configuration (46*b*) after executing the tube-joining operation; and a first tube detector (40) in communication with the controller (12), the first tube detector (40) being configured to generate a signal indicative of whether a first tube section (16 or 18) is present in the tube holder (14); wherein the controller (12) is configured to generate an instruction to return the tube holder (14) from the finish configuration (46*b*) to the start configuration (46*a*) when the first tube detector (40) generates a signal indicative of the first tube section (16 or 18) not being present.

According to the second aspect, the tube-joining device further comprises a blade (20) for cutting the tube sections (16, 18); and a heat source (36) in communication with the controller (12) that is configured to heat the blade (20); wherein the tube holder (14) has a clamped configuration (26*b*) whereby any flexible tube sections (16, 18) held in the tube holder (14) are clamped, and a non-clamped configuration (26*a*) whereby any flexible tube sections (16, 18) held in the tube holder (14) are not clamped; and wherein the controller (12) is configured to instruct the heat source (36) to automatically begin heating the blade (20) to a tube-joining temperature upon receipt of a signal that the tube holder (14) has changed from the non-clamped configuration (26*a*) to the clamped configuration (26*b*).

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 schematically illustrates a tube-joining device according to a principle of the present disclosure;

FIG. 2(*b*) illustrates the schematic example tube-joining device after joining flexible tube sections together;

FIG. 3(*b*) illustrates a cross-sectional view of an example tube holder in a clamped configuration;

FIG. 4(*b*) illustrates a cross-sectional view, perpendicular to that of FIGS. 3(*a*) and 3(*b*), of the tube holder and the blade after cutting tube sections;

FIG. 5(*b*) illustrates the tube holder in a finish configuration;

FIG. 6(*b*) shows an arrangement of the tube detectors and their alignment in a finish configuration;

FIG. 17(*a*) depicts an implementation of optional step G, which is to maintain the blade at a preheat temperature once the tube-joining device is switched on;

FIG. 17(*b*) depicts another implementation of optional step G, which is to maintain the blade at the tube-joining temperature once the tube-joining device is switched on;

Corresponding reference numerals indicate corresponding parts throughout the several views of the drawings.

DETAILED DESCRIPTION

Example embodiments will now be described more fully with reference to the accompanying drawings.

Figure 1:
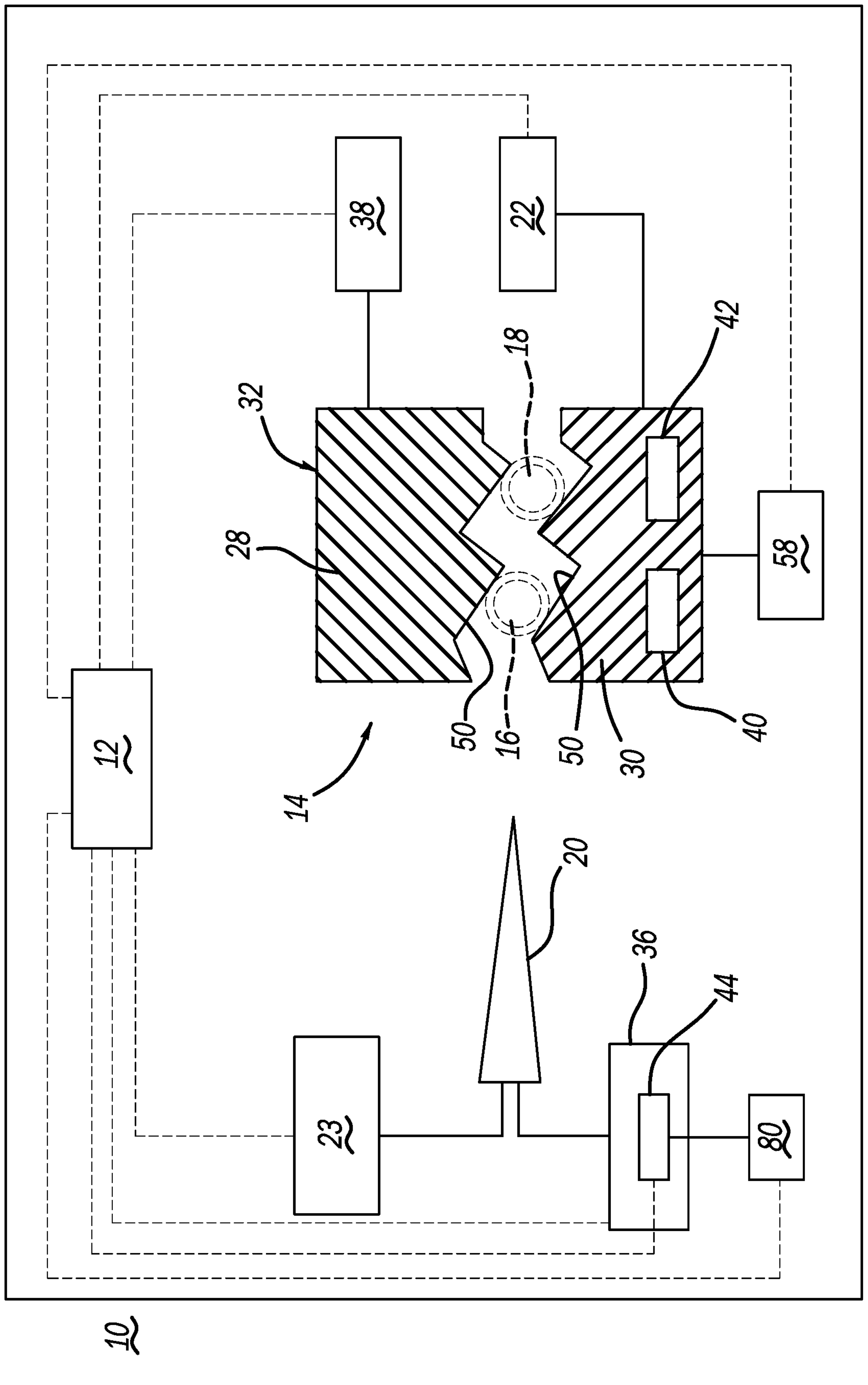

FIG. 1 schematically illustrates a tube-joining device 10 according to a principle of the present disclosure. Tube-joining device 10 may include features such as a controller 12, a tube holder 14 configured to hold a pair of flexible tube sections 16 and 18, a blade 20 for cutting tubes sections 16 and 18, and a motorized mechanism 22 for manipulating the tube holder 14 to rearrange the tubes 16, 18 cut by blade 20 so that the cut tube sections 16, 18 may subsequently connected to each other, as will be described later.

Figure 2A:
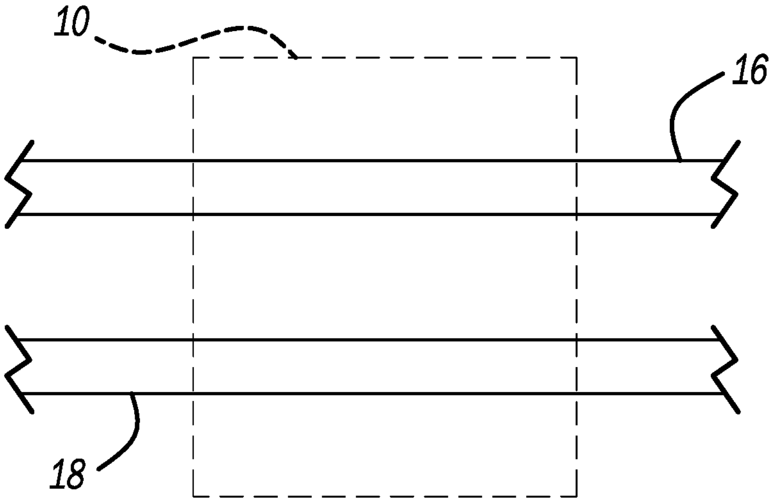
FIG. 2(*a*) illustrates a schematic example of a tube-joining device before joining flexible tube sections together.
Figure 2B:
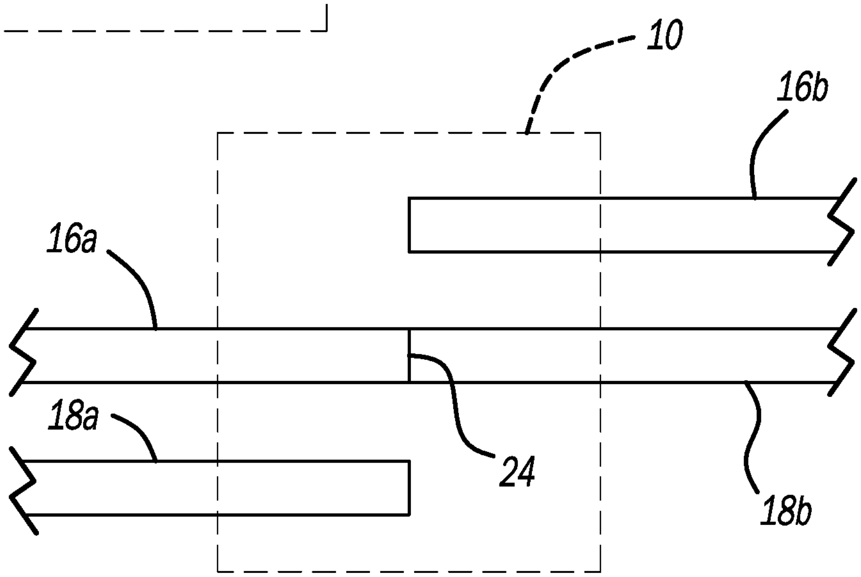

FIGS. 2(*a*) and 2(*b*) schematically illustrate tube-joining device 10 for joining together the two flexible tube sections 16 and 18, according to a principle of the present disclosure. As shown in FIG. 2(*a*), the two flexible tube sections 16, 18 are installed in the tube-joining device 10, preferably such that they are parallel to each other. Afterwards, the tube-joining device 10 may cut each of the flexible tube sections 16, 18. As will be explained in more detail later, this may be accomplished by pushing blade 20 across each of the flexible tube sections 16, 18. After cutting the flexible tube sections 16, 18, as shown in FIG. 2(*b*), the tube-joining device 10 may displace the flexible tube sections 16*a*, 18*a* on one side of the cut relative to the flexible tube sections 16*b*, 18*b* on the other side of the cut so that a cut face of one flexible tube section (e.g., tube section 16*a*) is aligned with a cut face of the other tube section (e.g., tube section 18*b*). As noted above, tube-joining device 10 may be provided with a motorized mechanism 22 for displacing the cut flexible tube sections 16*a*, 16*b*, 18*a*, 18*b*. More specifically, motorized mechanism 22 displaces a portion of tube holder 124 based on an instruction received from controller 12. The aligned cut faces may then be joined together, thereby joining the two flexible tube sections (e.g., cut tube section 16*a* to cut tube section 18*b*). If the two flexible tube sections 16, 18 are the tubes of two blood bags (17, 19—see FIG. 6) which are to be connected, then the tubes 16, 18 may be orientated such that portions 16*b* and 18*a* comprise the free ends of the respective tubes 16, 18.

Different approaches to displacing the cut flexible tube sections 16*a*, 16*b*, 18*a*, and 18*b* may be used. For example, the cut tube sections 16*a*, 18*a* on one side of the cut may be shifted linearly in a direction perpendicular to and coplanar with the axial direction of the two tubes 16*a*, 18*a*, which are parallel to each other. The linear shift may be achieved by a clamp having two halves, with each half holding one cut side of the tubes (i.e., one half of the clamp holds cut tube sections 16*a*, 18*a* and the other half of the clamp holds but tube sections 16*b*, 18*b*), and the relative linear position between the two halves may be changed using motorized mechanism 22. Specifically, one half may be stationary, and the other half may be shifted linearly. The cut tube sections (e.g., 16*a*, 18*a*) may be shifted by such an amount that the cut face of one tube (e.g., 16*a*) on one side of the cut aligns with the cut face of the other tube (e.g., 18*b*) on the other side of the cut. The aligned cut faces may then be brought together to form a joint 24.

Alternatively, the tubes (e.g., 16*a*, 18*a*) on one side of the cut may be moved to swap places by rotation through 180° by means of motorized mechanism 22 that is geared, so that the cut face of each of the two tubes (e.g., 16*a*, 18*a*) on one side of the cut aligns with the cut face of the other of the two tubes (e.g., 16*a* aligns with 18*b*, and 18*a* aligns with 16*b*) on the other side of the cut. The aligned cut faces may then be brought together to form the joint 24.

The flexible tube sections 16, 18 may be held securely in place by the tube-holding device 14. This may be achieved by clamping the flexible tube sections 16, 18. Clamping the flexible tube sections 16, 18 may involve pinching the tubes 16, 18. Optionally, the pinch may completely pinch the flexible tube 16, 18 so that, at the pinch-point, one side of the tube (e.g., an upper side) touches the other side (e.g., the lower side) of the tube so that no fluid may flow through the tube.

After the cut and during the displacement of the flexible tube sections 16, 18, it may be desirable to prevent blood (or another fluid) from flowing out at the cut faces. Therefore, during the cut and until the tubes 16, 18 are joined, clamping the flexible tube sections 16, 18 may involve pinching the tube on both sides of the cut, so as to stop fluid from flowing out of the tube at the cut ends.

Figure 3A:
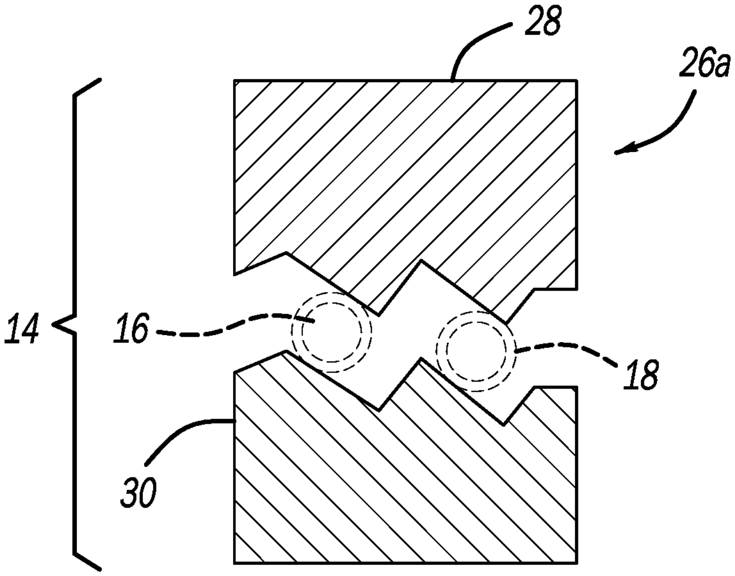
FIG. 3(*a*) illustrates a cross-sectional view of an example tube holder in a non-clamped configuration.
Figure 3B:
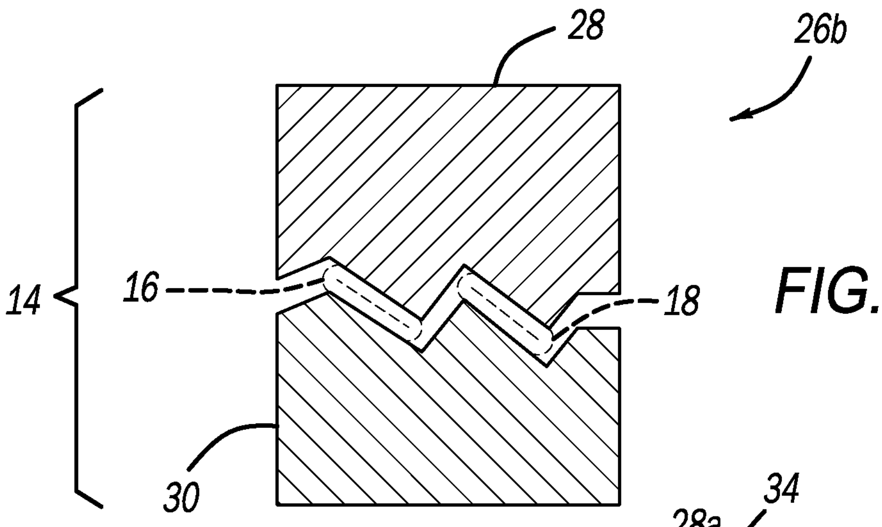

The clamping of the flexible tube sections 16, 18 is illustrated in FIGS. 3(*a*) and 3(*b*). FIGS. 3(*a*) and 3(*b*) show a cross-sectional view of tube holder 14 viewed from the axial direction of the flexible tube sections 16, 18. As shown in FIG. 1, tube holder 14 is part of the tube-joining device 10. The tube holder 14 may be configured to hold the flexible tube sections 16, 18 in place for joining.

The tube holder 14 may have a clamped configuration 26*b* (FIG. 3(*b*)), whereby any flexible tube sections 16, 18 held in the tube holder 14 are clamped. The tube holder 14 may have a non-clamped configuration 26*a* (FIG. 3(*a*)), whereby any flexible tube sections 16, 18 held in the tube holder 14 are not clamped. As shown in FIG. 3(*b*)(the clamped configuration), any flexible tube sections 16, 18 present may be clamped so as to hold the flexible tube sections 16, 18 securely in place. As shown, the tube holder 14 may comprise an upper part 28 and a lower part 30, and the flexible tube sections 16, 18 may be placed between the upper and lower parts 28, 30. The tube holder 14 may be put in the non-clamped configuration 26*a* by separating the upper and lower parts 28, 30. The tube holder 14 may be put in the clamped configuration 26*b* by bringing together the upper and lower parts 28, 30. As noted above, in the clamped configuration, the flexible tube sections 16, 18 may be pinched so that the flexible tube sections 16, 18 are closed, and any fluid present within the flexible tube sections 16, 18 may be prevented from flowing through the clamped portion of each flexible tube section 16, 18. Therefore, it should be understood that "clamping" may in general involve "pinching."

Figure 7:
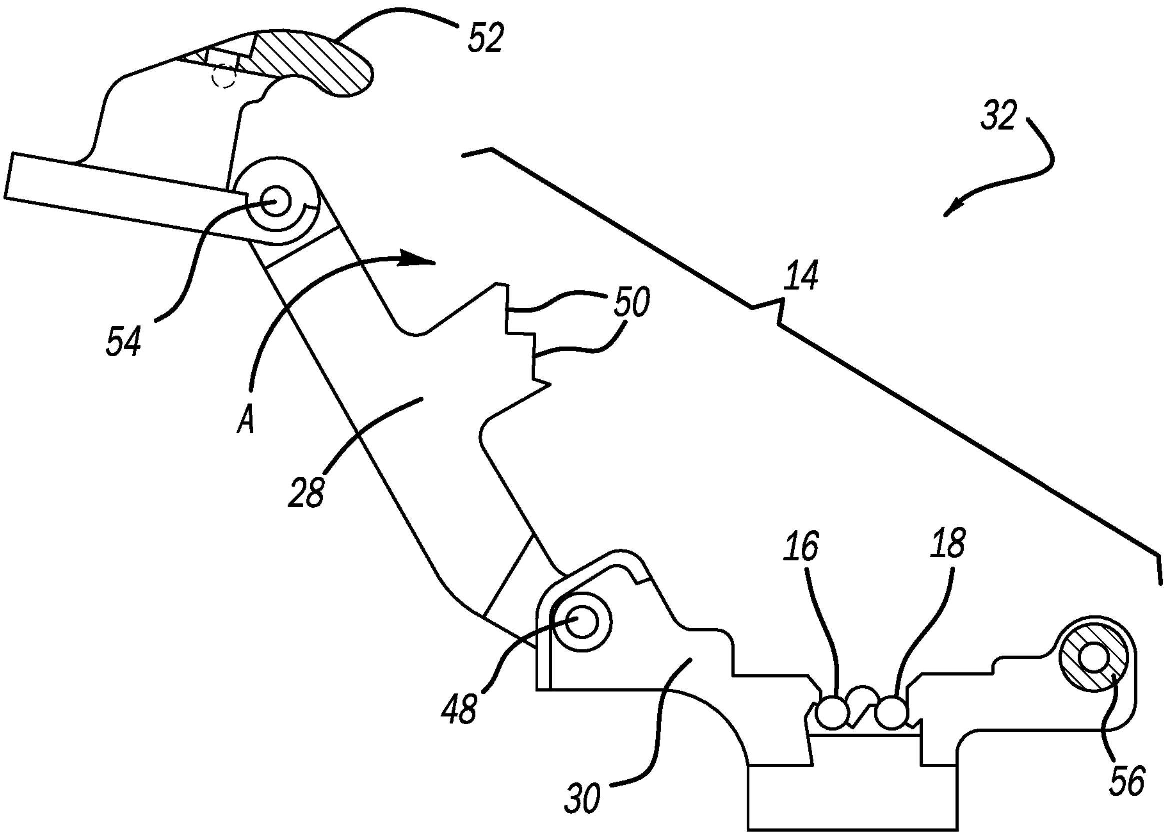
FIG. 7 illustrates a detailed example of the tube holder of FIGS. 3(*a*) to 5(*b*)

The clamping arrangement of tube holder 14 schematically shown in FIGS. 3(*a*) and 3(*b*) may correspond to the clamping arrangement shown in FIG. 7. In essence, the shift between the non-clamped 26*a* and clamped 26*b* configurations may be accomplished by manually closing a clamp 32 with portions 28, 30 that are shaped to keep the two flexible tube sections 16, 18 separated when located in the clamp 32.

Other ways of clamping tube sections 16, 18 can also be used. For example, a spring-loaded plunger (not shown) may be used to clamp the flexible tubes 16, 18. In such an arrangement, however, the tubes 16, 18 may not be kept separate from each other. In another example, a tube holder (not shown) having two slots configured for receipt of the flexible tubes 16, 18 may be used, and an electro-mechanical clamping element (not shown) may be provided within or as part of the slots to clamp or pinch the tubes 16, 18 shut.

Figure 4A:
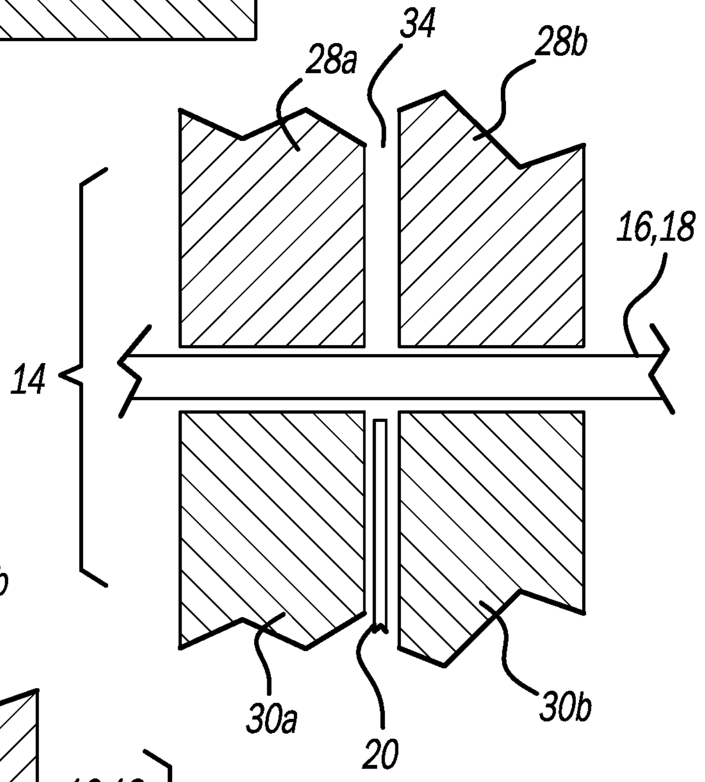
FIG. 4(*a*) illustrates a cross-sectional view, perpendicular to that of FIGS. 3(*a*) and 3(*b*), of the tube holder and a blade before cutting tube sections.
Figure 4B:
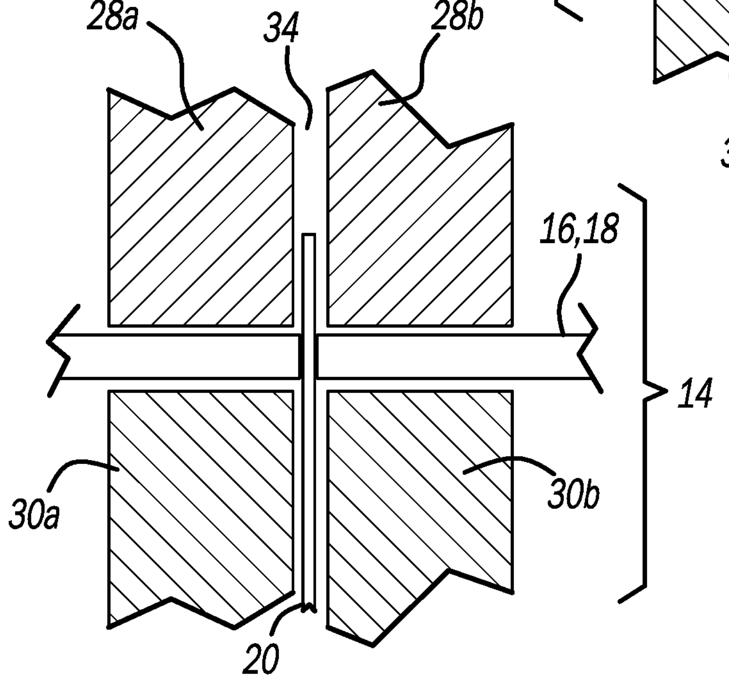

As noted above, the tube-joining device 10 may be configured to cut the flexible tube sections 16, 18 using a blade 20. This is best shown in FIGS. 4(*a*) and 4(*b*), which are cross-sectional views of the tube holder 14 in a direction perpendicular to the views shown in FIGS. 2 and 3. As shown in FIGS. 4(*a*) and 4(*b*), the flexible tube sections 16, 18 are shown being held in the tube holder 14 in the clamped configuration 26*b*. While only one flexible tube section (e.g., 16) is shown, it should be understood that a second flexible tube section (e.g., 18) may be present and held in the tube holder 14.

As shown in FIGS. 4(*a*) and 4(*b*), the upper part 28 of the tube holder 14 may be laterally divided into two halves 28*a*, 28*b* that are separated by a gap 34. Likewise, the lower part 30 of the tube holder 14 may also be divided into two halves 30*a*, 30*b* that are separated by a gap 34. This arrangement may be more intuitively conceptualized as two halves of the tube holder 14, a first half comprising 28*a* and 30*a*, and a second half comprising 28*b* and 30*b*. The first half 28*a*, 30*a* and the second half 28*b*, 30*b* of the tube holder 14 may move relative to each other (e.g., by motorized mechanism 22) so as to displace the flexible tube sections 16, 18 as illustrated in FIG. 2(*b*). The blade 20 may be provided within the gap 34. As shown in FIG. 4(*a*), the blade 20 may initially be hidden in the gap 34 such that it does not contact either of the flexible tube sections 16, 18 that may be present in the tube holder 14. To cut the flexible tube sections 16, 18, the tubes 16, 18 may be clamped as noted above to prevent leaking, and then the tube-joining device 10 may move the blade 20 using a blade actuator 23 through the gap 34 so that the blade 20 traverses the space where the flexible tube sections 16, 18 are held (as shown in FIG. 4(*b*)), thereby cutting the flexible tube sections 16, 18. Blade actuator 23 is configured to move blade 20 based on an instruction received from controller 12.

It should be understood that the tube-joining device 10 may be configured to heat the blade 20 up to a tube-joining temperature. The blade 20 may be heated by using, for example, a radiant or conductive heat source 36 that heats blade 20 based on an instruction received from controller 12. Alternatively or additionally, the blade 20 may be metallic, and may be heated using induction. Alternatively or additionally, the blade 20 may include an embedded resistive heating element (not shown), and the tube-joining device 10 may be configured to supply an electric current to the embedded resistive heating element based on an instruction received from controller 12. Upon contact with a flexible tube section 16, 18, the blade 20 can melt the flexible tube section 16, 18 and create two melted cut faces for each installed tube 16, 18, one on each side of the blade 20. After the flexible tube sections 16, 18 on one side of the blade 20 have been displaced (as explained above with reference to FIGS. 2(*a*) and 2(*b*)), the blade 20 may be withdrawn by actuator 23. Upon withdrawal, the melted cut face on one side of one flexible tube section 16, 18 may come into contact with the melted cut face on the other side of the other flexible tube section 16, 18, thereby forming the welded joint 24 (FIG. 2(*b*)).

The flexible tube sections 16, 18 may be formed of, for example, a thermoplastic material and the tube-joining temperature may be equal to or greater than the melting point of the material of the flexible tube sections 16, 18. That is, the tube-joining temperature should be at a temperature that is sufficient to melt an amount of the material of the flexible tube section 16, 18 to create a strong welded joint 24. The tube-joining temperature may be predefined and dependent on the material selected for forming the tube sections 16, 18. For example, the tube-joining temperature may be set at 180° C. or more, 220° C. or more, 260° C. or more, 300° C. or more, or 350° C. or less.

Conventionally, once the flexible tube sections 16, 18 have been installed into the tube holder 14, and the tube holder 14 put in the clamped configuration 26*b* (FIG. 3(*b*)), the operator of the tube holder 14 may be required to push a button so as to command the tube-joining device 10 to begin a tube-joining operation. In addition, prior to beginning a tube-joining operation, the operator may also have to push a button to begin heating the blade 20. Furthermore, after the tube-joining operation has completed, and after the operator has removed the joined tubes from the tube holder 14, the operator may be required to press a button to command the tube-joining device 10 to reset itself for the next tube-joining operation. Thus, conventionally, the operator is required to perform a large number of manual operations. While these operations may not be a large burden when a single tube-joining operation is performed, these operations can represent a significant source of inefficiency when a large number of tube-joining operations are to be performed. Therefore, in order to reduce the operational burden on the operator, and thereby save time and operating expense, at least some of these manual operations can be automated through use of controller 12.

In view of the above, the present disclosure is directed to a tube-joining device 10 that may automatically start a tube-joining operation to join the two flexible tube sections 16, 18 when the tube holder 14 is in the clamped configuration 26*b*. Therefore, the operator is not required to press a button to command the tube-joining device 10 to begin a tube-joining operation.

The term "automatically" is generally used in this application to refer to an absence of input from an operator. For example, the pressing of a button may be omitted. However, the term "automatically" may not necessarily imply that an operation is carried out immediately without delay, and may not necessarily preclude taking into account other factors. For example, the tube-joining device 10 may be configured such that the tube-joining operation is prevented from being started until certain other criteria are met. For example, the tube-joining device 10 may automatically start the tube-joining operation only when certain other criteria are met in addition to the tube holder 14 being in the clamped configuration 26*b*.

In order to trigger a tube-joining operation, the tube-joining device 10 may comprise a sensor 38 (see, e.g., FIG. 1) in communication with controller 12 for detecting whether the tube holder 14 is in the clamped configuration 26*b*. Any suitable sensor known to one skilled in the art may be used. For example, the sensor 38 may be a push switch, a Hall-effect sensor, an optical switch, a magnetic switch, an inductive sensor, or a capacitive sensor.

The tube-joining device 10 may additionally detect whether a first tube section 16, 18 is present in the tube holder 14. The tube-joining device 10 may comprise a first tube detector 40 (FIG. 1) in communication with controller 12, with the first tube detector 40 being configured to detect a first tube section 16 or 18 in tube holder 14. Controller 12, based on a signal received from the first tube detector 40, may prevent the tube-joining device 10 from starting the tube-joining operation until the first tube detector 40 detects the presence of a first tube section 16 or 18. In other words, the tube-joining device 10 may be configured to automatically start a tube-joining operation to join the two flexible tube sections 16, 18 when the tube holder 14 is in the clamped configuration 26*b* and the first tube detector 40 detects the presence of a first tube section 16 or 18, and communicates the presence of the first tube section 16 or 18 to controller 12. The first tube detector 40 may comprise any suitable sensor. For example, the sensor of first tube detector 40 may be a push switch, a Hall-effect sensor, an optical switch, a magnetic switch, an inductive sensor, or a capacitive sensor.

The tube-joining device 10 may additionally detect whether a second tube section 16 or 18 is present in the tube holder 14. The tube-joining device 10 may comprise a second tube detector 42 (FIG. 1) in communication with controller 12, with the second tube detector 42 being configured to detect a second tube section 16 or 18. Controller 12, based on a signal received from the second tube detector 42, may prevent the tube-joining device 10 from starting the tube-joining operation until the second tube detector 42 detects the presence of a tube section 16 or 18. In other words, the controller 12 may be configured to automatically start a tube-joining operation to join the two flexible tube sections 16, 18 when the tube holder 14 is in the clamped configuration 26*b*, the first tube detector 40 detects the presence of a first tube section 16 or 18, the second tube detector 42 detects the presence of a second tube section 16 or 18, and each detector 40, 42 transmits a corresponding signal to controller 12. It should be understood that references to "first" and "second" tube sections or tube detectors are merely labels and do not imply any particular order or other kinds of hierarchy. Similar to first tube detector 40, second tube detector 42 may comprise any suitable sensor such as, for example, a push switch, a Hall-effect sensor, an optical switch, a magnetic switch, an inductive sensor, or a capacitive sensor.

A reason for detecting the presence of a first tube 16 and/or a second tube 18 is that it can be used as an indication to controller 12 that the tube-joining device 10 is ready to perform a tube-joining operation. Therefore, the tube-joining operation may begin without requiring the operator to press a button. This may simplify the operations to be performed by the operator, and may thus also save time.

A reason for using the presence of two tubes as an indication to start the tube-joining process is to prevent the tube-joining device 10 from performing a tube-joining operation when no tube 16, 18 or only one tube (e.g., 16) is present. If the tube-joining operation proceeds without both tubes 16, 18 present, no tubes would be joined, resulting in time and energy being wasted. Furthermore, any consumables necessary for tube-joining operations would also have been wasted.

The tube-joining device 10 may comprise a temperature monitor 44 for monitoring the temperature of the blade 20. Temperature monitor 44 may be part of heat source 36 (as shown in FIG. 1), or may be separate therefrom. Any suitable temperature monitor 44 may be used. For example, the temperature monitor 44 may comprise a thermistor, a resistance temperature detector, a thermocouple, a semiconductor-based sensor, or an infrared sensor. Controller 12, based on a signal indicative of the temperature of blade 22 received from temperature monitor 44, may be configured to prevent the tube-joining device 10 from starting the tube-joining operation until the temperature of the blade 20 reaches the desired tube-joining temperature. In other words, the controller 12 may be configured to automatically start a tube-joining operation to join the two flexible tube sections 16, 18 when the tube holder 14 is in the clamped configuration 26*b* and the temperature monitor 44 detects that the blade 20 has reached the tube-joining temperature. Alternatively, controller 12 may be configured to automatically start a tube-joining operation to join the two flexible tube sections 16, 18 when the tube holder 14 is in the clamped configuration 26*b*, and one or both of the first and second tube detectors 40, 42 detects the presence of one or both of the first and second tube sections 16, 18, and the temperature monitor 44 detects that the blade 20 has reached the tube-joining temperature.

By ensuring that a temperature of blade 20 has reached the tube-joining temperature before performing a tube-joining operation, faulty or weak tube joints 24 may be prevented. Specifically, as explained above, the purpose of the blade 20 is not only to cut the flexible tubes 16, 18, but also to melt a material of the tube sections 16, 18. If the temperature of the blade 20 is insufficient, the tubes 16, 18 would not be sufficiently melted, and the joint 24 will not be properly formed when the cut faces (e.g., 16*a* and 18*b*) of the tubes 16, 18 are brought together.

Figure 5A:
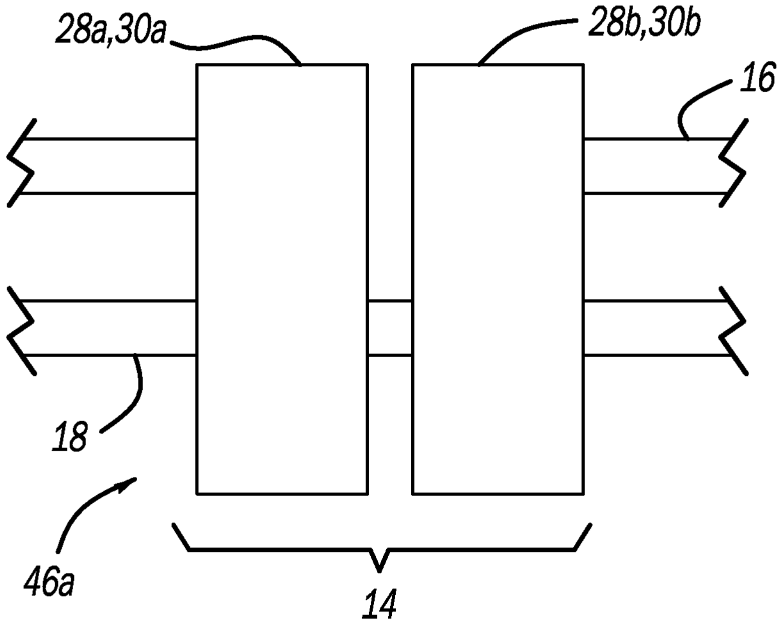
FIG. 5(*a*) illustrates the tube holder in a start configuration.
Figure 5B:
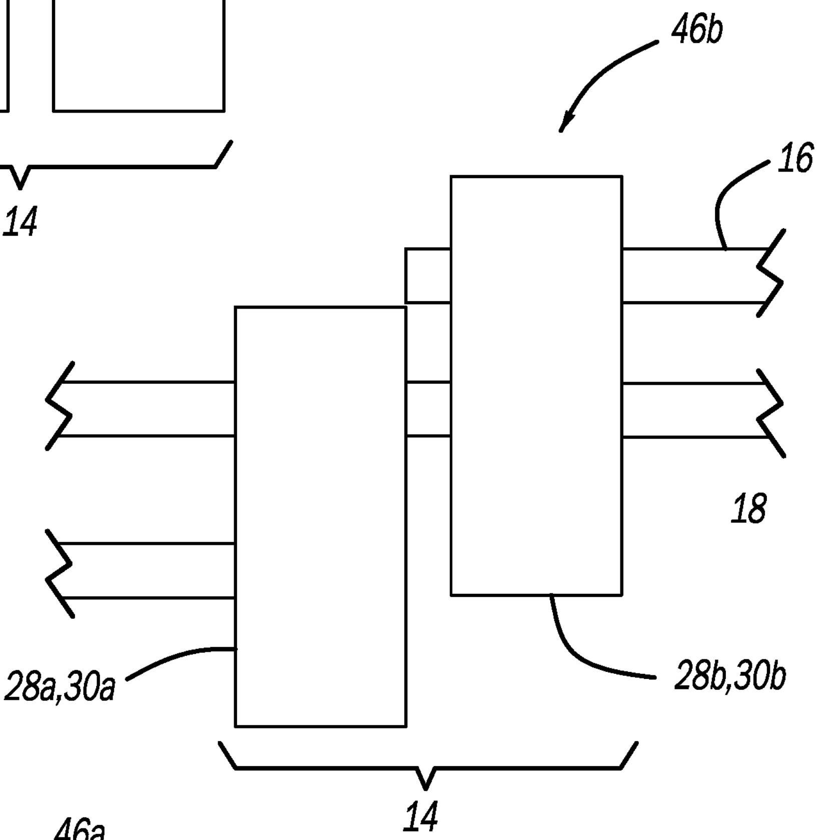
Figure 6A:
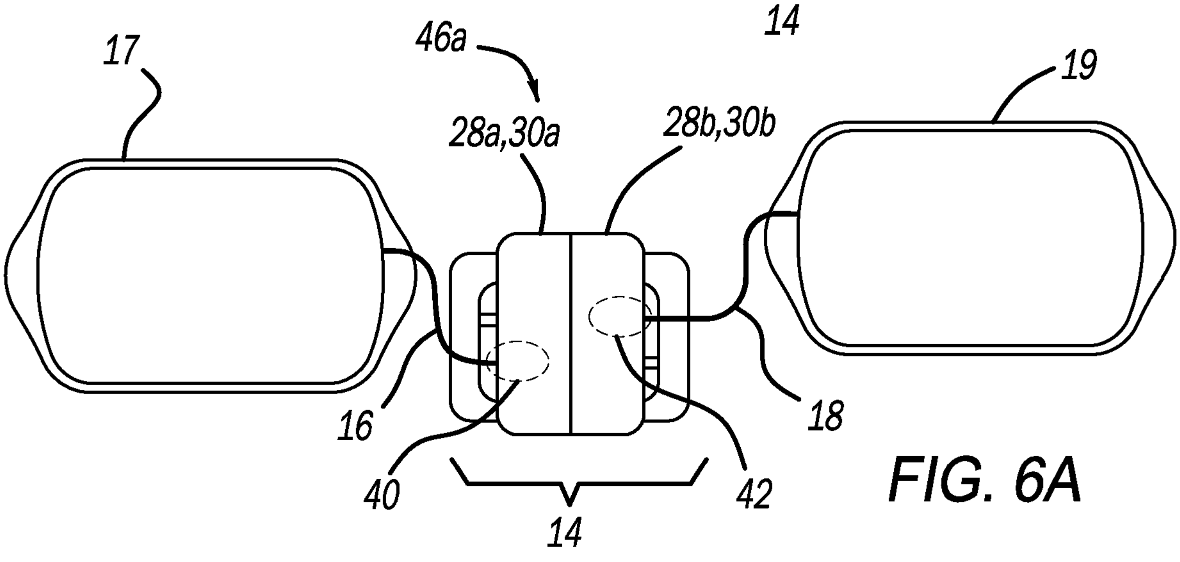
FIG. 6(*a*) shows an arrangement of tube detectors and their alignment in a start configuration.
Figure 6B:
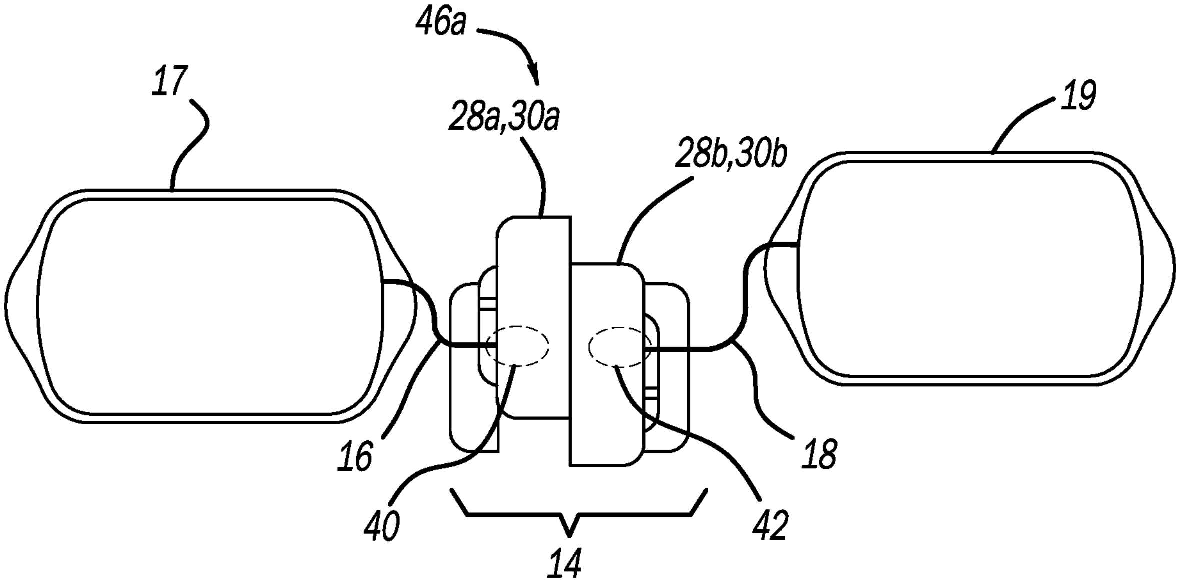

In addition to the clamped 26*b* and non-clamped 26*a* configurations, the tube holder 14 may, as shown in the examples of FIGS. 5(*a*) and 5(*b*) and FIGS. 6(*a*) and 6(*b*), have a start configuration 46*a* (FIGS. 5(*a*) and 6(*a*)) and a finish configuration 46*b* (FIGS. 5(*b*) and 6(*b*)). The start configuration 46*a* may be one in which the first half 28*a*, 30*a* and the second half 28*b*, 30*b* of the tube holder 14 are aligned. The finish configuration 46*b* may be one in which the first half 28*a*, 30*a* and/or the second half 28*b*, 30*b* are displaced away from the aligned position. The tube holder 14 may be in the start configuration 46*a* before executing a tube-joining operation, and in the finish configuration 46*b* after executing the tube-joining operation.

As described above, the tube-joining device 10 may include tube detectors 40, 42 that are configured to detect whether tube sections 16, 18 are present in the tube holder 14. As best shown in FIGS. 6(*a*) and 6(*b*), in the start configuration 46*a*, tube detectors 40 and 42 may be positioned to detect two different tubes 16, 18, and in the finish configuration 46*b* the tube detectors 40 and 42 may be configured to detect the same joined tube.

The tube detectors 40, 42 may be located on opposite sides of the blade 20 (not shown in FIGS. 6(*a*) and 6(*b*)). Specifically, the first tube detector 40, which is configured to detect the first tube 16, may be located proximate the first tube 16 which will form the joined tube, and the second tube detector 42, which is configured to detect the second tube 18, may be located proximate the second tube 18 which will form the joined tube.

The first tube detector 40 may be provided on the first half 28*a*, 30*a* of the tube holder 14 at a location where the portion of the first tube 16 that will form part of the joined tube will be inserted, and the second tube detector 42 may be provided on the second half 28*b*, 30*b* of the tube holder 14 at a location where the portion second tube 18 that will form part of the joined tube will be inserted. As shown in FIG. 1, tube detectors 40 and 42 communicate with controller 12 and on the basis of signals received from detectors 40, 42, controller 12 may initiate or prevent the tube-joining operation.

When the tube holder 14 is in the finish configuration 46*b* and the first tube detector 40 detects that the first tube section 18 is not present, controller 12 may instruct tube holder 14 to return from the finish configuration 46*b* to the start configuration 46*a*. Controller 12 may additionally prevent the return of the tube holder 14 from the finish configuration 46*b* to the start configuration 46*a* until the second tube detector 42 also detects that the second tube section 18 is not present. As noted above, in the finish configuration 46*b*, both the first and second tube sections 16, 18 may be parts of the same joined tube. The return to the start configuration 46*a* may be automatic. Therefore, in practice, after the tube-joining device 10 has completed a tube-joining operation, and the operator removes a flexible tube section 16, 18 from the tube holder 14, the controller 12 may initiate a reset so that the tube holder 14 is in the starting configuration 46*a*, ready for the next tube-joining operation.

Again referring to FIGS. 5(*a*) and 5(*b*), as the tube holder 14 moves between the start configuration 46*a* and the finish configuration 46*b*, the first half 28*a*, 30*a* may be stationary and the second half 28*b*, 30*b* may move. Alternatively, the first half 28*a*, 30*a* may move, and the second half 28*b*, 30*b* may be stationary. Alternatively, both halves may move in opposite directions. Although FIGS. 5(*a*) and 5(*b*) show that the relative movement between the first half 28*a*, 30*a* and the second half 28*b*, 30*b* is in a particular direction, the relative movement may be in a direction opposite to that which is shown in FIGS. 5(*a*) and 5(*b*). In other words, by controller 12 initiating a reset after the detection of the absence of a first tube 16 by tube detector 40, there is no need for the operator to press a button in order to prepare the tube-joining device 10 for the next tube-joining operation. This simplifies the operations to be performed by the operator, and may thus also save time in successive tube-joining operations.

As discussed above, in the clamped configuration 26*b*, the flexible tube sections 16, 18 may be closed (e.g., pinched), and any fluid present within the flexible tube sections 16, 18 may be prevented from flowing through the clamped portion of each flexible tube section 16, 18. In the non-clamped configuration 26*a*, the flexible tube sections 16, 18 may be open. The tube holder 14 may be configured to be in the clamped configuration 26*b* by a manual operation. The tube holder 14 may be configured to be in the non-clamped configuration 26*a* by a manual operation. Specifically, the tube holder 14 may comprise the clamp 32 shown in FIG. 7.

As shown in FIG. 7, the upper part 28 and the lower part 30 may be connected at a hinge 48. The clamp 32 may be biased towards the non-clamped configuration 26*a*, such as by a spring (not shown). With the clamp 32 of FIG. 7, the manual operation for configuring the tube holder 14 in the clamped configuration 26*b* may include closing the clamp 32 by pivoting upper part 28 in the direction of arrow A, whereupon shaped portions 50 of the clamp 32 keep the flexible tube sections 16, 18 separate while they are clamped shut. To maintain upper part 28 in a clamped arrangement with lower part 30, clamp 32 may include a latch 52 that is pivotably connected to upper part 28 by a pivot pin 54. When upper part 28 is pivoted toward lower part 30, latch 52 may be engaged with a tubular member 56 connected to lower part 30. Conversely, the manual operation for configuring the tube holder 14 in the non-clamped configuration 26*b* may include detaching the latch 52 from tubular member 56 and pivoting upper part 28 away from lower part 30 to open the clamp 32.

The manual operation above may be assisted by a motorized mechanism 58 that communicates with controller 12. For example, the clamp 32 may be closed most of the way (e.g., 95%) manually, and the motorized mechanism 58 may complete the remainder (e.g., 5%) of the closing of the clamp 32. An example motorized mechanism 58 may include a cam and a follower.

Figure 8:
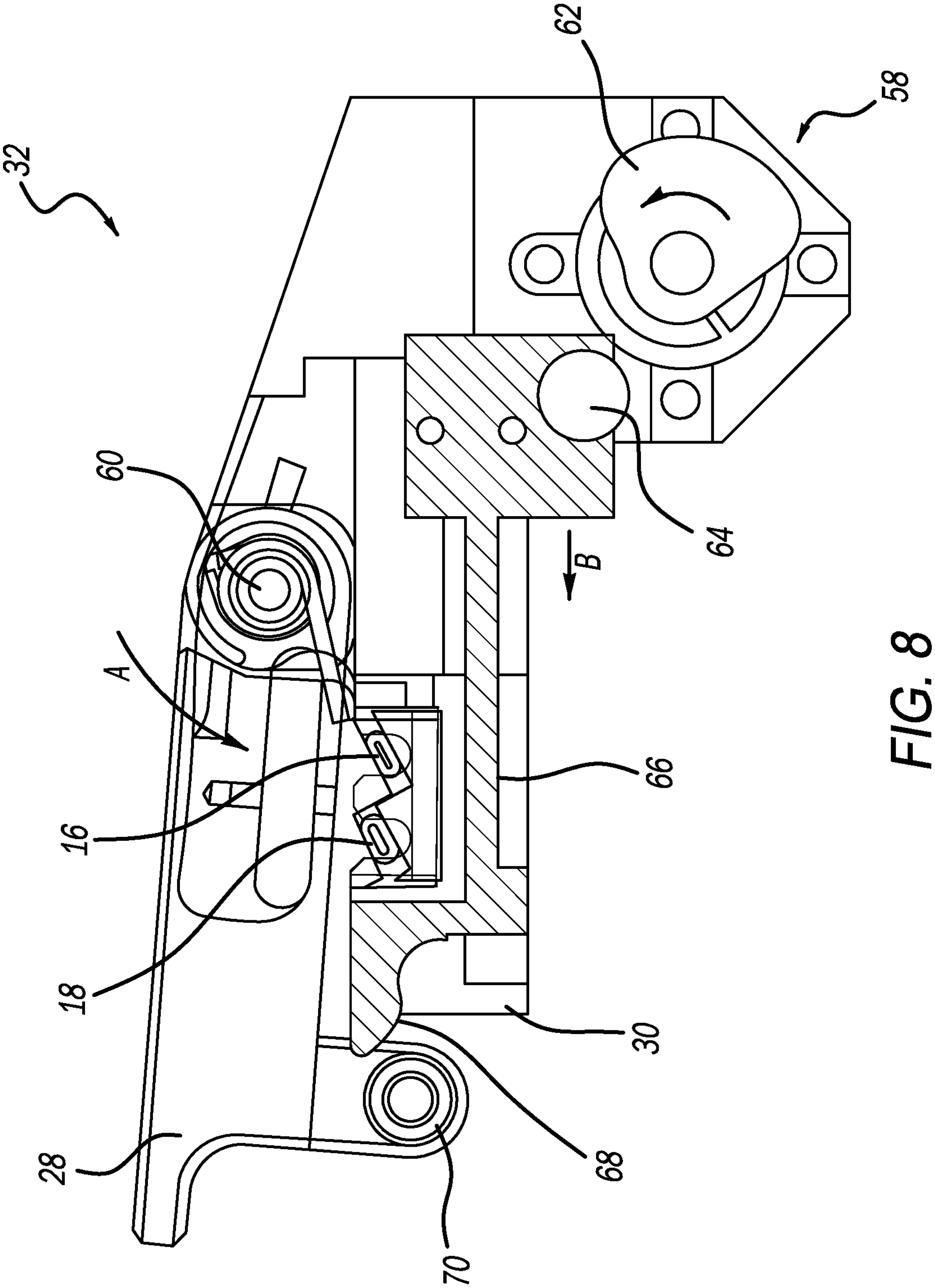
FIG. 8 shows another detailed example of the tube holder of FIGS. 3(*a*) to 5(*b*)

This may be achieved using the arrangement shown in FIG. 8. As shown, the clamp 32 may be hinged at hinge 60. A cam 62 may be provided on the lower part 30 of the clamp 32. A follower 64 may be rotatably provided at one end of a slider 66 slidably housed in the lower part 30 of the clamp 32. Although not shown in FIG. 8, the slider 66 may be biased towards the cam 62. On the other end of the slider 66, a latch portion 68 may be included. The upper part 28 may be provided with a roller 70 configured to engage with the latch portion 68. The clamp 32 may be configured to detect whether the clamp 32 has been closed (via sensor 38) to a predetermined position at which time motorized mechanism 58 is triggered.

Based on a signal received from sensor 38 that is communicated to controller 12, controller 12 is configured to trigger the motorized mechanism 58 such that the cam 62 is rotated to engage with the follower 64. The cam 62 may be profiled such that it pushes the follower 64 away (in direction of arrow B) when engaging with follower 64. The movement of the follower 64 causes the slider 66 to slide linearly, causing the latch portion 68 to move in the same direction (B). The latch portion 68 may then engage the roller 70. The latch portion 68 may be shaped so that, as it engages the roller 70, it causes the upper part 28 to move towards the lower part 30, thereby further closing the clamp 32. The controller 12 may be configured to detect (via signals received from motorized mechanism 58) when the clamp 32 is in the fully clamped configuration 26*b*, and accordingly stop the motorized mechanism 58.

While in the fully clamped configuration 26*b*, the motorized mechanism 58 may prevent the clamp 32 from being opened manually due to the engagement of the latch portion 68 and the roller 70. This may prevent an operator from opening the clamp 32 when a tube-joining operation is in progress.

To release the clamp 32 from the fully clamped configuration 26*b*, the motorized mechanism 58 may rotate cam 62 in an opposite direction so as to cause or allow the slider 66 to retract, thereby causing the latch portion 68 to disengage from the roller 70. As noted above, the slider 66 may retract due to the biasing towards the cam 62. This may allow the upper part 28 of the clamp 32 to move away from the lower part 30 of the clamp 32. The controller 12 may be configured to detect (via signals received from motorized mechanism 58 or sensor 38) when the clamp 32 has been opened to the above predetermined position. At the predetermined position, the clamp 32 may be freely opened manually.

Figure 9:
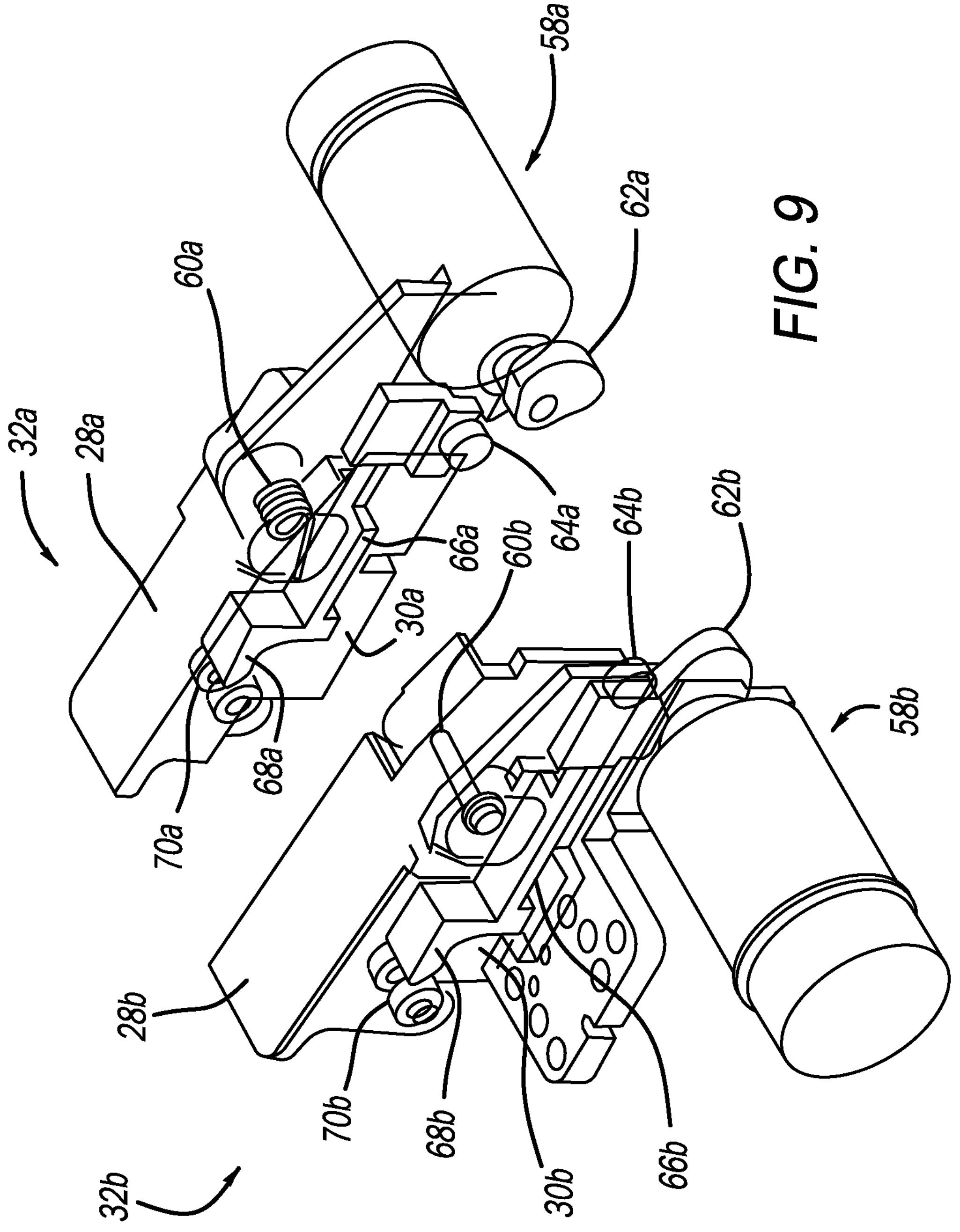
FIG. 9 shows further detail of the tube holder of FIG. 8.

As noted above, the tube holder 14 may be divided into two halves. As shown in FIG. 9, the clamp 32 described above may be divided into two halves 32*a*, 32*b*. Each half 32*a*, 32*b* of the clamp 32 may include a respective divided half of each of the elements described above, namely an upper part 28*a*, 38*b*, a lower part 30*a*, 30*b*, a hinge 60*a*, 60*b*, a cam 62*a*, 62*b*, a follower 64*a*, 64*b*, a slider 66*a*, 66*b*, and a roller 70*a*, 70*b*. As shown, each half 32*a*, 32*b* of the clamp 32 may be provided with its own motor 58*a*, 58*b* driving the respective cam 62*a*, 62*b*. A gearbox (not shown) may be provided to reduce the speed and increase the torque of the motor 58*a*, 58*b* driving the respective cam 62*a*, 62*b*. The gearbox may include a planetary gear mechanism, or the gearbox may include other suitable mechanisms such as a worm drive mechanism.

The tube-joining device 10 may be configured to dispose of the blade 20 after each execution of the tube-joining operation. The tube-joining device 20 may use a new blade 20 for each execution of the tube-joining operation. While tubes 16, 18 are clamped and closed during the tube-joining operation, the likelihood that blade 20 comes into contact with any fluid held in the bags may be reduced. Nonetheless, even though there is a reduced likelihood of the blade 20 contacting a fluid in tubes 16, 18, use of a new blade 20 each time a tube-joining operation is conducted may be advantageous to prevent any risk of contamination between the bags of fluid in one tube-joining operation due to residues from a previous tube-joining operation.

In practice, after the tube-joining device 10 has completed a tube-joining operation and the operator removes a flexible tube section 16, 18 from the tube holder 14, the controller 12 may initiate an automatic reset so that the tube holder 14 is in the starting configuration 46*a*, ready for the next tube-joining operation. The controller 12 may alternatively, or in addition to any of the combinations of features described in the foregoing disclosure, be configured to automatically instruct heat source 36 to begin heating a blade 20 up to a tube-joining temperature when the tube holder 14 changes from the non-clamped 26*a* to the clamped 26*b* configuration.

Automatically beginning to heat the blade 20 may be advantageous because it simplifies the manual steps carried out by the operator. It may also be time-saving because heating may begin without waiting for an input from the operator (e.g., pushing a button). Receipt by controller 12 of a signal indicative of a change from the non-clamped 26*a* to the clamped 26*b* configuration from sensor 38 may provide a suitable indication that a tube-joining operation is about to begin, at which point controller 12 may instruct heat source 36 to begin heating of the blade 20.

The tube-joining device 10 disclosed hereinabove may also be configured to preheat the blade 20. Specifically, controller 12 may be configured to instruct heat source 36 to heat the blade 20 so as to maintain the blade 20 at a preheat temperature. The controller 12 may instruct heat source 36 to maintain this preheat temperature when the tube-joining device 10 is in an idle state. An idle state may be a state in which controller 12 is awaiting an input from one of its sensors. The tube-joining device 10 may be in an idle state as soon as it is switched on. The preheat temperature may be a temperature below the tube-joining temperature. For example, the preheat temperature may be at least about 40° C., about 60° C., about 80° C., about 100° C., or up to about 120° C. Keeping the blade 20 at the preheat temperature may provide further time-saving because it may reduce the time it takes to heat the blade 20 up to the tube-joining temperature.

Alternatively, controller 12 may be configured to instruct heat source 36 to heat the blade 20 so as to constantly maintain the blade 20 at the tube-joining temperature. In this regard, controller 12 may instruct heat source 36 to begin supplying heat to blade 20 as soon as tube-joining device 10 is switched on, or may await an input from the operator before beginning to heat the blade 20 up to the tube-joining temperature. Keeping the blade 20 at the tube-joining temperature may provide further time-saving as the tube-joining device 10 will not have to spend time in an idle state while the blade 20 heats up to the tube-joining temperature.

As discussed above, controller 12 may be configured to instruct heat source 36 to automatically begin heating the blade 20 up to a tube-joining temperature when the tube holder 14 changes from the non-clamped 26*a* to the clamped 26*b* configuration. As an alternative, controller 12 may be configured to instruct heat source 36 to automatically begin heating the blade 20 up to a tube-joining temperature when the controller 12 receives a signal that indicates that tube holder 14 has transitioned from the clamped 26*b* to the non-clamped 26*a* configuration. In other words, in practice, when the operator causes the tube holder 14 to shift into the non-clamped configuration 26*a*, controller 12 may instruct heats source 36 such that automatic heating may begin. For example, with reference to the example of FIG. 7, the operator may manually open the clamp 32, and controller 12 can instruct heat source to automatically begin heating. It should be understood, however, that if the clamp 32 is provided with a motorized mechanism 58 as discussed above with reference to FIG. 8, the operator may cause the tube holder 14 to shift from the (fully) clamped configuration 26*b* by pressing a button. This may cause the motorized mechanism 58 to release the clamp 32, at which point automatic heating may begin. Alternatively, controller 12 may be configured to automatically release the clamp 32 by means of the motorized mechanism 58 subject to a predetermined trigger, after which the automatic heating may begin.

After the tube holder 14 has changed from the clamped 26*b* to the non-clamped 26*a* configuration, the controller 12 may be configured to verify that (or pause until) a used blade 20 has cooled down and has been ejected before beginning heating again. The signal indicative that blade 20 has cooled may be generated by temperature monitor 44 and transmitted to controller 12. The detection that the used blade 20 has cooled down may also serve as a trigger to automatically release the clamp 32.

A new blade 20 may also be put in place. The controller 12 may be configured to delay instructing heat source 36 to begin heating until the new blade 20 is in place. The tube-joining device 10 may include a motorized mechanism (not shown) for ejecting and/or putting in place blades 20, or may be configured to allow blades 20 to be ejected and/or put in place manually by an operator. This may provide further time-saving because a detection of the non-clamped configuration 26*a* by controller 12 may indicate that a previous tube-joining operation has finished, and the operator is about to start joining the next set of flexible tube sections 16, 18. For example, after a tube-joining operation, the operator may set the tube holder 14 in the non-clamped configuration 26*a*, remove the flexible tube sections 16, 18 that have been joined, and install new flexible tube sections 16, 18 for another tube-joining operation. Therefore, the controller 12 may advantageously make use of the time in which the operator removes and installs flexible tube sections 16, 18 by instructing heat source 36 to heat the blade 20. In other words, based on a signal received by controller 12 that indicates that a change from the clamped 26*b* to the non-clamped configuration 26*a* has occurred (i.e., an indication that a previous tube-joining operation has finished), controller 12 may instruct heat source 36 to begin heating the blade 20 in anticipation for the next tube-joining operation. Time-savings can be seen when a sequence of tube-joining operations are performed in succession.

As noted above, the tube-joining device 10 may include tube detectors 40, 42 (FIGS. 1 and 6) configured to detect whether first tube section 16 and second tube section 18 are located in tube holder 14. The tube detectors 40, 42 may prevent controller 12 from instructing heat source 36 to begin heating the blade 20 up to the tube-joining temperature until the tube detectors 40, 42 detects whether the tubes 16, 18 are present. In other words, based on a signal generated by the tube detectors 40, 42 and received by controller 12 that tubes 16, 18 have not been inserted into tube holder 14, controller 12 may not instruct heat source 36 to begin heating of the blade 20 until controller 12 receives a signal from tube detectors 40, 42 that indicates that the flexible tube sections 16, 18 have been inserted by the operator. The blade 20 may initially be at room temperature or may be maintained at a preheat temperature described above. This may have the advantageous effect of avoiding unnecessary heating of the blade 20.

When one of the detectors 40 or 42 generates a signal indicative of the operator having installed at least one tube 16 or 18 into tube holder 14, the signal may be used by controller 12 as an indication that a tube-joining operation may be about to begin. At this time, controller 12 may instruct heat source 36 to begin heating of blade 20 in anticipation of the second tube 16 or 18 being installed and a tube-joining operation being conducted. This may eliminate the need for the operator to press a button in order to begin heating the blade 20, and may also save time because the temperature of the blade 20 may be near or equivalent to the tube-joining temperature by the time the tube-joining operation begins. The amount of time during which the tube-joining device 11 is idle while the blade 31 is heated may therefore be reduced or even eliminated.

It should be understood, however, that because the insertion of tubes 16, 18 is performed by the operator, it may be unpredictable how much time there will be between the insertion of a first tube 16 or 18 and the insertion of a second tube 16 or 18. Therefore, if controller 12 were to instruct heat source 36 to begin heating of blade 20 as soon as a first tube 16 or 18 is inserted, there is a chance that the blade 20 will remain heated for a long time before the second tube 16 or 18 is inserted and before the tube-joining operation begins. During this time, energy is wasted as heat radiates from the blade 20 into the environment for no apparent benefit. Therefore, the insertion of two tubes 16 and 18 may be a more reliable indication that a tube-joining operation is about to begin, and an associated advantage is that energy is less likely to be wasted.

If, after the first tube 16 or 18 (and optionally the second tube 16 or 18) has been installed and the controller 12 has instructed heat source 36 to begin heating the blade 20 up to the tube-joining temperature, the operator removes the first tube 16 or 18 and/or the second tube 16 or 18 for whatever reason (e.g., the operator realizes that a wrong tube is inserted, a tube is removed inadvertently, etc.), the controller 12 may immediately instruct heat source 36 to stop the heating of blade 20 until receiving a signal from detector 40 or 42 that a first tube 16 or 18 (and optionally a second tube 16 or 18) has been installed again.

Furthermore, in the event that the blade 20 is formed of a material having a limited tolerance for heat, it should be understood that the blade 20 may become unusable if maintained at the tube-joining temperature for too long of a time period. Therefore, by delaying the onset of heating until two tubes 16 and 18 have been inserted, the blade 20 is less likely to become overheated and unusable.

To address this effect, the controller 12 may be configured to monitor (via temperature monitor 44) and limit the time period for which the blade 20 is maintained at the tube-joining temperature. This may be achieved by controller 12 instructing heat source 36 to only heat the blade 20 for a limited duration, which limited duration is less than a duration after which the blade 20 becomes unusable.

A timer 80 in communication with both temperature monitor 44 and controller 12 may be provided to record the accumulated amount of time during which a blade 20 has been heated. The timer 80 may be arranged to record time only when the temperature of the blade 20 exceeds a threshold (e.g., the tube-joining temperature). The duration of a tube-joining operation may be predetermined through testing of the system 10, and the blade 20 may be maintained at the tube-joining temperature throughout the tube-joining operation. Therefore, a time limit for preheating outside the tube-joining operation may be determined by subtracting the known duration of the tube-joining operation from the limited duration in which the blade 20 may be maintained at the tube-joining temperature without becoming unusable. The controller 12 may be configured to instruct heat source 36 to stop preheating blade 20 once the time limit is reached.

The controller 12 may also be configured, after the execution of a tube-joining operation to join the two flexible tube sections 16, 18, to automatically instruct heat source 36 to stop heating the blade 20. This instruction from controller 12 can be sent to heat source 36 immediately after the tube-joining operation. The controller 12 may continue to instruct heat source 36 to not to heat any blade 20 (to the tube-joining temperature or any other elevated temperature) until the tube-joining device 10 is ready to perform a new tube-joining operation. The used blade 20 may be discarded after each tube-joining operation, and a new blade 20 may then be installed. For example, the heat source 36 may heat the new blade 20 by being instructed to do so in response to controller 12 receiving a signal from one of the sensors 38 or detectors 40, 42. The disclosure above provides numerous examples of arrangements wherein the tube-joining device 10 is caused to automatically heat the blade 20 in response to some detection. Stopping the heating of the blade 20 to the tube-joining (or another) temperature after the tube-joining operation may avoid heating the blade 20 unnecessarily.

Figure 10:
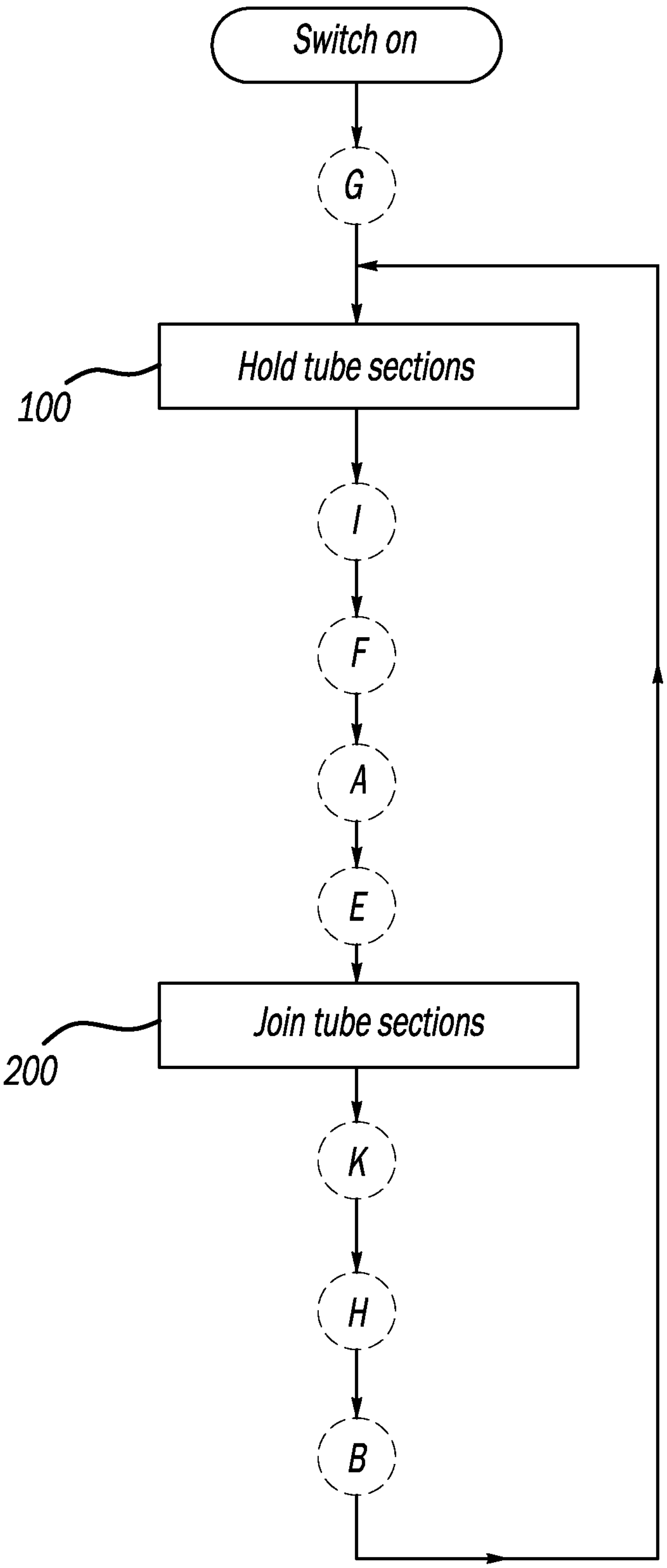
FIG. 10 shows a general sequence of steps of a tube-joining operation performed by a tube-joining device, with optional steps A, B, E, F, G, H, I and K.

In addition to the above-described tube-joining device 10, the present disclosure is also directed to a tube-joining method for joining two flexible tube sections 16, 18. With reference to FIG. 10, the method may comprise the steps of holding (i.e., at step 100 in FIG. 10), in a tube holder 14 of a tube-joining device 10, the flexible tube sections 16, 18 in place for joining, and executing a tube-joining operation (i.e., at step 200 in FIG. 10) to join the two flexible tube sections 16, 18. The method may be repeated so that successive sets of flexible tube sections 16, 18 may be joined.

As noted above, tube holder 14 may have a clamped configuration 26*b* and a non-clamped configuration 26*a*, may have a start configuration 46*a* and a finish configuration 46*b*, and may have a blade 20 for cutting the flexible tube sections 16, 18. The tube-joining device 10 may include heat source 36 that is configured, based on an instruction received from controller 12, to heat the blade 20 for melting the flexible tube sections 16, 18. Accordingly, FIG. 10 also shows a number of possible additional steps G, I, F, A, E, K, H, B, which may include automatic steps.

Figure 11:
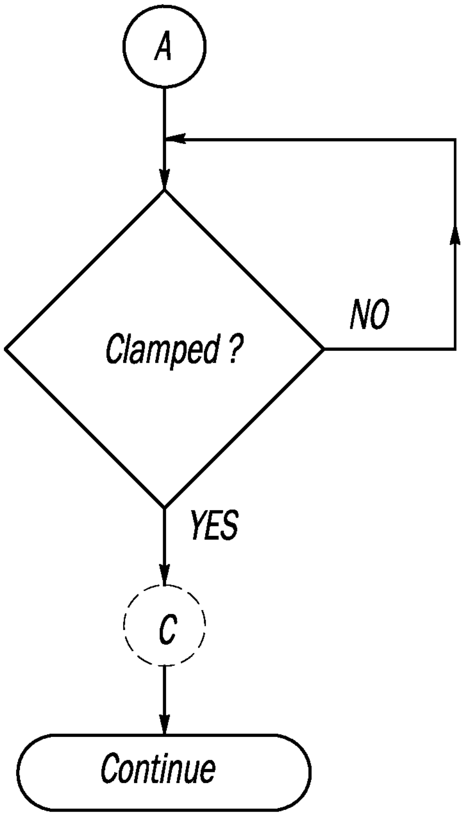
FIG. 11 depicts optional step A, which is to automatically start a tube-joining operation upon detection of a clamped configuration, followed by optional step C.

With reference to FIG. 11, the step of executing the tube-joining operation 200 to join the two flexible tube sections 16, 18 may be conditional upon detecting that the tube holder 14 is in the clamped configuration 26*b* (step A). In this case, the tube-joining operation 200 may be executed automatically. This may simplify the manual operations to be performed by the operator, and also save time.

Figure 12:
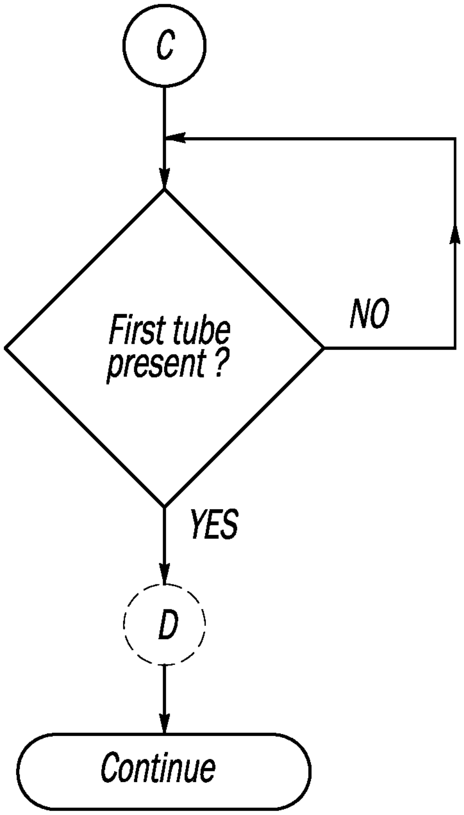
FIG. 12 depicts optional step C, which is to pause the method until a first tube is present, followed by optional step D.

The automatic execution of the tube-joining operation 200 may be prevented by the conditions in step C. With reference to FIG. 12, step C may include pausing the tube-joining operation 200 until the detection of a first tube section 16 or 18 by detectors 40, 42. This may prevent the tube-joining operation 200 from beginning when no tube 16 or 18 is present.

Figure 13:
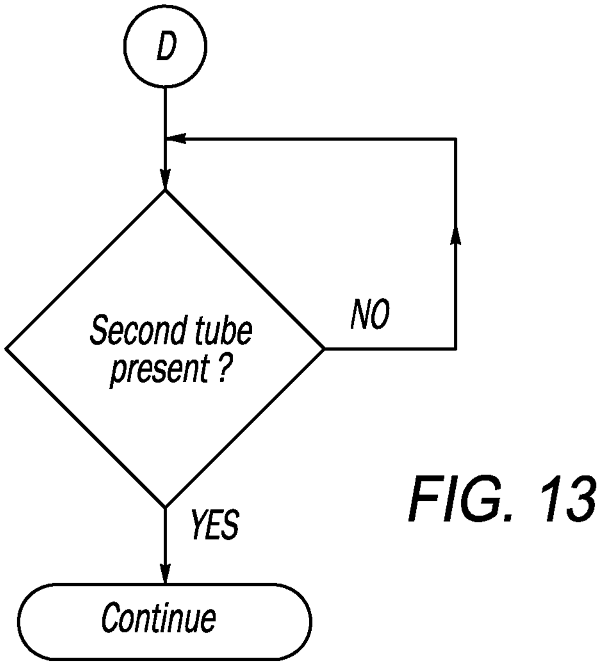
FIG. 13 depicts optional step D, which is to pause the method until a second tube is present.

Step C may include a step D. With reference to FIG. 13, step D may include pausing the tube-joining operation 200 until the detection of a second tube section 16 or 18 by detectors 40 or 42. This may prevent the tube-joining operation 200 from beginning when only one tube 16 or 18 is present. As noted above, when no tube 16 or 18 or only one tube 16 or 18 is present, no tube would be joined by the tube-joining operation 200, thereby wasting time and energy.

Figure 14:
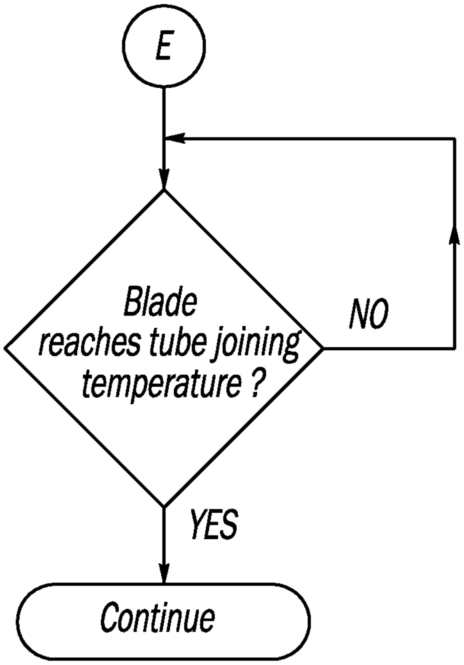
FIG. 14 depicts optional step E, which is to automatically start a tube-joining operation upon detecting that the blade has reached a tube-joining temperature.

With reference to FIGS. 10 and 14, the tube-joining operation 200 may be preceded by a step E of pausing the tube-joining operation 200 until the blade 20 reaches the tube-joining temperature disclosed above. After the pause, the tube-joining operation 200 may be executed automatically. As explained above, this may prevent faulty or weak tube joints 24 from being produced.

Figure 15:
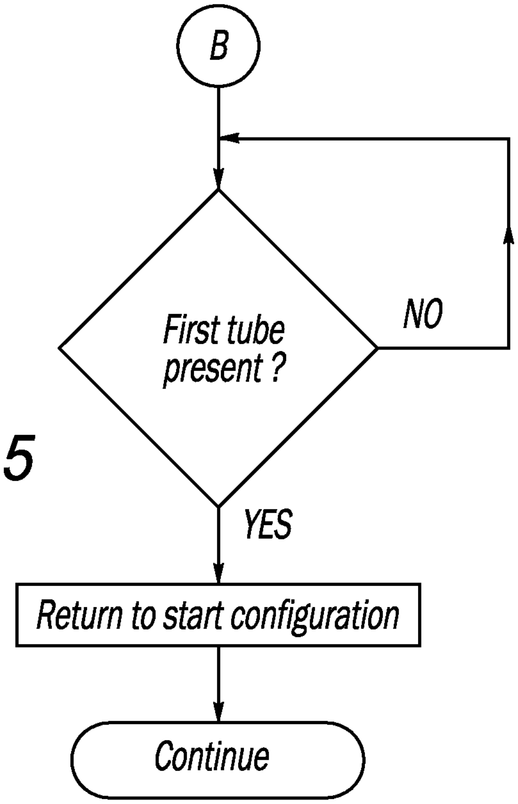
FIG. 15 depicts optional step B, which is to automatically return the tube holder to the start configuration upon detecting that the first tube is not present.

With reference to FIG. 15, as explained above, after the tube-joining operation 200, the tube holder 14 may be in the finish configuration 46*b*. The method may include, after executing the tube-joining operation 200, the step of automatically returning the tube holder 14 to the start configuration 46*a*. However, the step of automatically returning the tube holder 14 to the start configuration 46*a* may be paused until a detection by detectors 40 or 42 that a first tube section 16 or 18 is absent. A detection of the absence of a first tube section 16 or 18 at this point may indicate that the tube-joining operation 200 has finished, and the operator has removed the first tube section 16 or 18 from the tube holder 14 in preparation for the next tube-joining operation. Resetting the tube holder 14 at this point, without the operator pressing a button, may therefore simplify the operations performed by the operator, and thus also save time.

Figure 16:
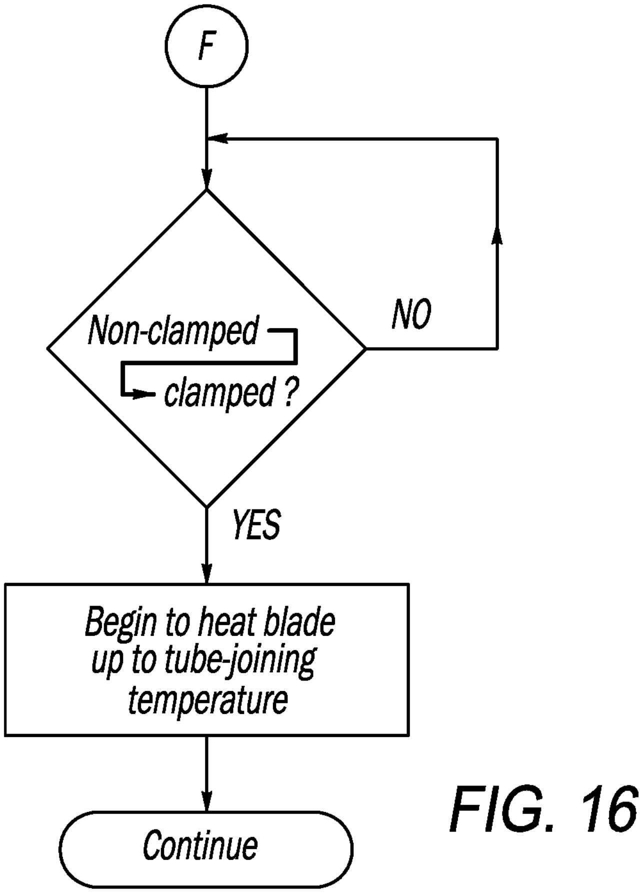
FIG. 16 depicts optional step F, which is to automatically begin to heat the blade up to the tube-joining temperature upon detecting a change from the non-clamped to the clamped configuration.

With reference to FIG. 16, the method may include the step of automatically beginning to heat the blade 20 up to the tube-joining temperature before executing the tube-joining operation 200. The step of automatically beginning to heat the blade 20 up to the tube-joining temperature may not be executed until the tube holder 14 changes from the non-clamped configuration 26*a* to the clamped configuration 26*b*. As noted above, this change may indicate that a tube-joining operation 200 is about to begin, and thus heating of blade 20 may begin upon detecting this change so as to save time.

Figure 17A:
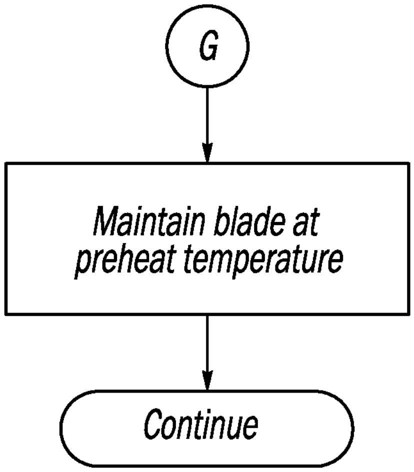
Figure 17B:
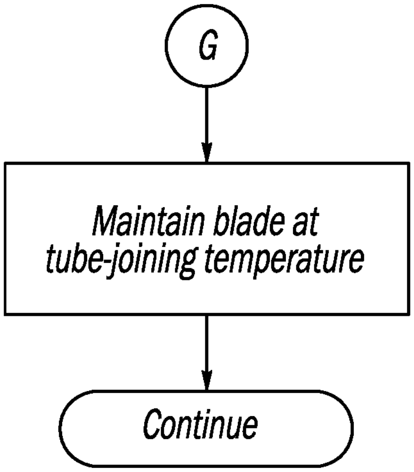

With reference to FIG. 17*a*, after the tube-joining device 10 has been switched on, the blade 20 may be heated and maintained at the preheat temperature as disclosed above. Alternatively, with reference to FIG. 17*b*, after the tube-joining device 10 has been switched on, the blade 20 may be heated and maintained at the tube-joining temperature. As noted above, preheating the blade 20 may reduce the time needed to heat the blade 20 up to the tube-joining temperature, whereas maintaining the blade 20 at the tube-joining temperature may eliminate any waiting time entirely.

Figure 18:
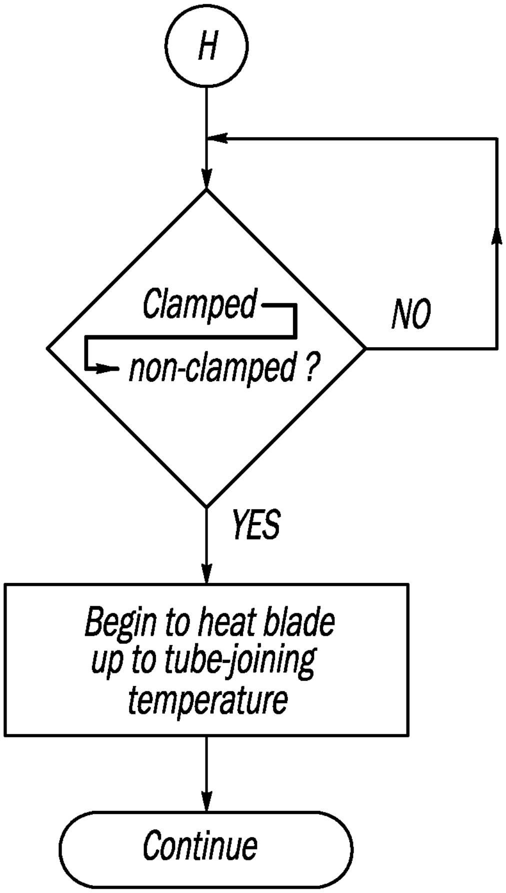
FIG. 18 depicts optional step H, which is to begin to heat the blade up to the tube-joining temperature upon detecting a change from the clamped to the non-clamped configuration.

With reference to FIG. 18, the method may include, after the tube-joining operation 200, the step of automatically beginning to heat the blade 20 up to the tube-joining temperature. The step of automatically beginning to heat the blade 20 up to the tube-joining temperature may be not executed until the tube holder 14 changes from the clamped configuration 26*b* to the non-clamped configuration 26*a*. As noted above, this change of configuration corresponds to the operator (or the controller 12, if tube-joining device 10 is equipped with the motorized mechanism 58 described above with reference to FIG. 8) releasing the tube holder 14 from the clamped configuration 26*b*, and serve as an indication that the tube-joining operation 200 has finished, which indication may be used to predict that the next tube-joining operation 200 is about to begin. At this point, a used blade 20 may be present, and the used blade 20 may still be hot. Therefore, the step of automatically beginning to heat the blade 20 may be delayed until the used blade 20 has cooled down and been ejected. Typically, the used blade 20 will cool down sufficiently within a few seconds for ejection. After ejecting the used blade 20, a new blade 20 may be put in place. The new blade 20 may be put in place manually or automatically by a motorized mechanism of the tube-joining device 10. Similarly, the ejection of the used blade 20 may be carried out manually or automatically by a motorized mechanism of the tube-joining device 10. Heating the blade 20 at this point therefore anticipates the next tube-joining operation 200, thereby saving time.

As noted above with reference to FIG. 8, the tube holder 14 may comprise a clamp 32 with a motorized mechanism 58 for assisting the closing of the clamp 32. The motorized mechanism 58 may also be configured to lock the clamp 32 in the clamped configuration 26*b* until the clamp 32 is released. In this case, the above step of automatically beginning to heat the blade 20 may be delayed beyond a detection that the tube holder 14 (i.e., the clamp 32) has been released from the clamped configuration 26*b* by the motorized mechanism 58, and until the controller 12 receives a signal indicative of the clamp 32 being or has been opened manually by the operator.

Figure 19:
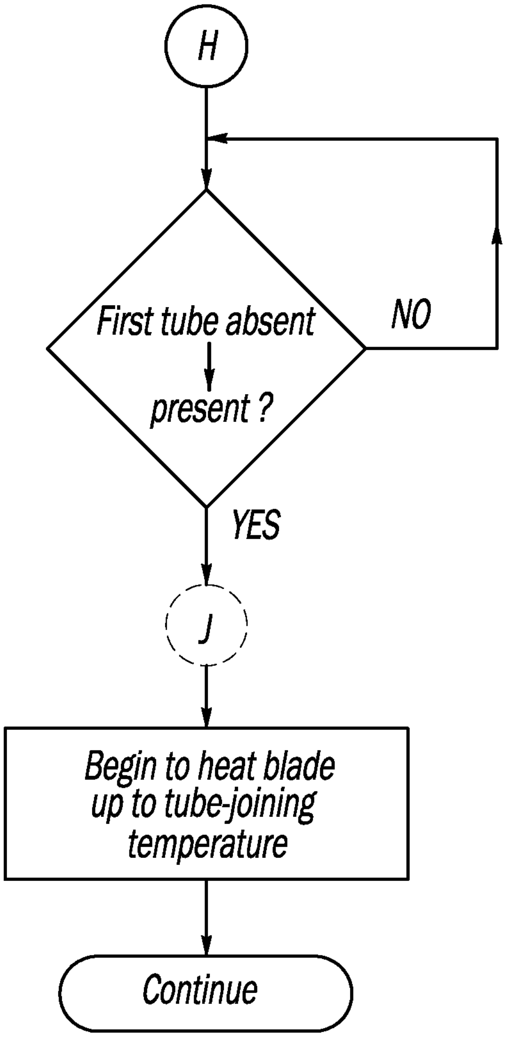
FIG. 19 depicts optional step I, which is to automatically begin to heat the blade up to the tube-joining temperature upon detecting a change from a first tube being absent to being present, with option step J to be performed after detecting said change and before heating the blade.

With reference to FIG. 19, the method may include, before the tube-joining operation 200, the step of automatically beginning to heat the blade 20 up to the tube-joining temperature. The step of automatically beginning to heat the blade 20 up to the tube-joining temperature may not begin until a detection of a change from a first tube 16 or 18 being absent to being present. This may happen in practice when the operator installs the first tube 16 or 18 into the tube holder 14. This may be used as an indication that a tube-joining operation 200 is about to begin, and thus heating of blade 20 may begin without operator input.

Figure 20:
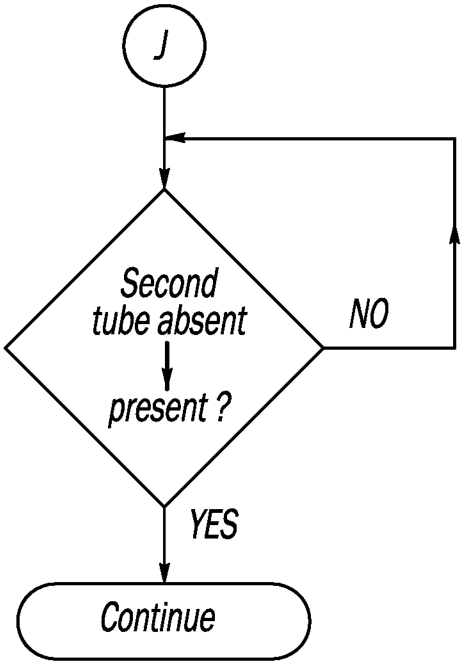
FIG. 20 depicts optional step J, which is to pause until detecting a change from a second tube being absent to being present.

The step of automatically beginning to heat the blade 20 up to the tube-joining temperature may be preceded by step J. With reference to FIG. 20, step J may include pausing until a detection of a change from a second tube 16 or 18 being absent to being present. This may happen in practice when the operator installs the second tube 16 or 18 into the tube holder 14. As noted above, the insertion of two tubes 16, 18 may be a more reliable indicator that a tube-joining operation 200 is about to begin.

Figure 21:
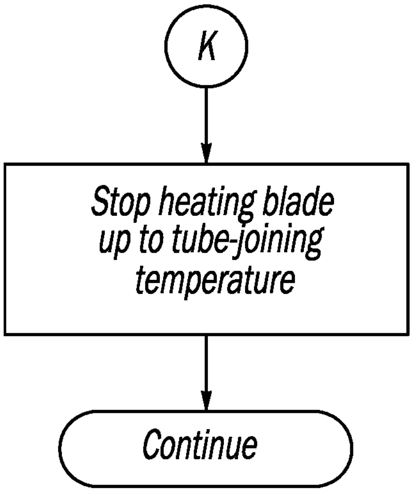
FIG. 21 depicts optional step K, which is to stop heating the blade up to the tube-joining temperature immediately after a tube-joining operation.

With reference to FIG. 21, the method may include, immediately after the tube-joining operation 200, a step of stopping heating of the blade 20 up to the tube-joining temperature. It should be understood that heating may begin again when the tube-joining device 10 is next caused to begin heating the blade 20 again.

In the device and method disclosed above, the tube-joining operation 200 may further comprise locking the tube holder 14 in the clamped configuration 26*b* until the flexible tube sections 16, 18 have been joined. This may prevent an operator from configuring the tube holder 14 to the non-clamped configuration 26*a* when a tube-joining operation 200 is in progress. Otherwise, if the tube holder 14 is shifted to the non-clamped configuration 26*a* during a tube-joining operation 200 when the tubes 16, 18 are either cut or not yet securely joined, fluid in the tubes 16, 18 may leak out. This not only requires subsequent cleaning the tube-joining device 10, but may also lead to potential contamination of the blood or other fluid contained in the blood bag(s), which may be wasted as a result.

The locking of the tube holder 14 may be automatic, and may be achieved by a motorized mechanism (e.g., 58) or an electro-mechanical means. The locking may be achieved by the motorized mechanism 58 disclosed above with reference to FIG. 8. The locking may alternatively be achieved by activating an electromagnet.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tube-joining device for joining two flexible tube sections, the device comprising:

a controller;

a tube holder configured to hold the flexible tube sections in place for joining, the tube holder having a clamped configuration wherein any flexible tube sections held in the tube holder are clamped;

a blade that is configured to cut the flexible tube sections; and a heat source in communication with the controller, wherein the heat source is configured to pre-heat the blade and maintain a temperature of the blade at a pre-heat temperature; and wherein upon receipt by the controller of a signal indicative of the tube-joining device being in the clamped configuration, the controller is configured to automatically start a tube-joining operation to join the two flexible tube sections where the heat source raises the temperature of the blade from the pre-heat temperature to a tube-joining temperature based on an instruction received from the controller.

2. The tube-joining device of claim 1, wherein the tube holder further comprises a first tube detector in communication with the controller that is configured to generate a signal indicative of whether a first tube section is present in the tube holder; and wherein the controller upon receipt of the signal from the first tube detector that the first tube section is present in the tube holder and the signal indicative of the tube-joining device being in the clamped configuration is configured to start the tube-joining operation.

3. The tube-joining device of claim 2, wherein the tube holder comprises a second tube detector in communication with the controller that is configured to generate a signal indicative of whether a second tube section is present in the tube holder; and wherein the controller upon receipt of the signal from the second tube detector that the second tube section is present in the tube holder and the signal indicative of the tube-joining device being in the clamped configuration is configured to start the tube-joining operation.

4. The tube-joining device of claim 3, wherein the first and second tube detectors are located proximate the tube holder such that, after the tube-joining operation, each of the first and second tube detectors are configured to generate a signal indicative of a presence of a joined tube.

5. The tube-joining device of claim 1, further comprising a temperature monitor in communication with the controller and configured to generate a signal indicative of a temperature of the blade; and wherein the controller is configured to prevent the tube-joining device from starting the tube-joining operation until receiving the signal indicative of the temperature of the blade from the temperature monitor that the temperature of the blade is at the tube-joining temperature.

6. The tube-joining device according to claim 1, wherein the tube holder is configured to be in a start configuration before executing a tube-joining operation, and wherein the tube holder is configured to be in a finish configuration after executing the tube-joining operation;

wherein the tube-joining device comprises a first tube detector in communication with the controller that is configured to generate a signal indicative of whether a first tube section is present in the tube holder; and wherein the controller is configured to instruct a motorized mechanism to return the tube holder from the finish configuration to the start configuration when the first tube detector generates a signal indicative of the first tube section not being present.

7. The tube-joining device of claim 1, wherein the tube holder is configured to be in the clamped configuration by a manual operation.

8. The tube-joining device of claim 7, wherein the tube holder comprises a clamp, and the manual operation includes closing the clamp.

9. The tube-joining device of claim 1, wherein the controller is configured to instruct a motorized mechanism to move the tube holder to be in the clamped configuration automatically after the controller has received a signal indicative that flexible tube sections are located in the tube holder.

10. A tube-joining device for joining two flexible tube sections, the device comprising:

a controller;

a tube holder configured to hold the flexible tube sections in place for joining, wherein the tube holder is configured to be in a start configuration before executing a tube-joining operation, and wherein the tube holder is configured to be in a finish configuration after executing the tube-joining operation;

a blade that is configured to cut the flexible tube sections;

a heat source in communication with the controller, wherein the heat source is configured to pre-heat the blade and maintain a temperature of the blade at a pre-heat temperature; and a first tube detector in communication with the controller, the first tube detector being configured to generate a signal indicative of whether a first tube section is present in the tube holder;

wherein the controller is configured to automatically start a tube-joining operation to join the two flexible tube sections where the heat source raises the temperature of the blade from the pre-heat temperature to a tube-joining temperature based on an instruction received from the controller; and wherein the controller is configured to generate an instruction to return the tube holder from the finish configuration to the start configuration when the first tube detector generates a signal indicative of the first tube section not being present.

11. The tube-joining device of claim 10, wherein the tube holder has a clamped configuration whereby any flexible tube sections held in the tube holder are clamped, and a non-clamped configuration whereby any flexible tube sections held in the tube holder are not clamped; and wherein the controller is configured to instruct the heat source to automatically begin raising the temperature of the blade to the tube-joining temperature upon receipt of a signal that the tube holder has changed from the non-clamped configuration to the clamped configuration.

* * * * *